United States Patent
Tatara

(10) Patent No.: US 11,129,529 B2
(45) Date of Patent: Sep. 28, 2021

(54) OPHTHALMOLOGIC APPARATUS AND METHOD OF CONTROLLING THE SAME

(71) Applicant: TOPCON CORPORATION, Tokyo (JP)

(72) Inventor: Yoko Tatara, Kita-ku (JP)

(73) Assignee: TOPCON CORPORATION, Tokyo (JP)

(*) Notice: Subject to any disclaimer, the term of this patent is extended or adjusted under 35 U.S.C. 154(b) by 201 days.

(21) Appl. No.: 16/432,965

(22) Filed: Jun. 6, 2019

(65) Prior Publication Data

US 2020/0046220 A1 Feb. 13, 2020

(30) Foreign Application Priority Data

Aug. 9, 2018 (JP) .............................. JP2018-150530

(51) Int. Cl.
*A61B 3/10* (2006.01)
*A61B 3/032* (2006.01)
(Continued)

(52) U.S. Cl.
CPC ............ *A61B 3/102* (2013.01); *A61B 3/0016* (2013.01); *A61B 3/0091* (2013.01); *A61B 3/032* (2013.01);
(Continued)

(58) Field of Classification Search
CPC ....... A61B 3/102; A61B 3/032; A61B 3/0016; A61B 3/0091; A61B 3/14; A61B 3/1225; A61B 3/103; A61B 3/12
(Continued)

(56) References Cited

U.S. PATENT DOCUMENTS 10,028,655 B2* 7/2018 Fujii .................... A61B 3/0091
10,791,922 B2* 10/2020 Hayashi ................. A61B 3/102
(Continued)

FOREIGN PATENT DOCUMENTS

CN 103222851 A 7/2013
CN 103381091 A 11/2013
(Continued)

OTHER PUBLICATIONS

Extended European Search Report dated Dec. 18, 2019 in European Application No. 19180242.0.
(Continued)

*Primary Examiner* — Mohammed A Hasan
(74) *Attorney, Agent, or Firm* — Xsensus LLP

(57) ABSTRACT

An ophthalmologic apparatus includes a refractometry optical system, an OCT optical system, a fixation projection system, and a controller. The refractometry optical system is configured to project light onto a subject's eye and to detect returning light from the subject's eye. The OCT optical system is configured to split light from an OCT light source into measurement light and reference light, to project the measurement light onto the subject's eye, and to detect interference light between returning light of the measurement light from the subject's eye and the reference light. The fixation projection system is configured to simultaneously project a first fixation target and a second fixation target onto the subject's eye, a visual angle of the second fixation target being narrower than a visual angle of the first fixation target. The controller is configured to control the refractometry optical system and the OCT optical system to simultaneously perform a refractometry and an OCT measurement.

10 Claims, 11 Drawing Sheets

(51) Int. Cl.
    *A61B 3/00*     (2006.01)
    *A61B 3/14*     (2006.01)
    *A61B 3/12*     (2006.01)
    *A61B 3/103*     (2006.01)

(52) U.S. Cl.
    CPC ............ *A61B 3/103* (2013.01); *A61B 3/1225* (2013.01); *A61B 3/14* (2013.01)

(58) Field of Classification Search
    USPC ........................................................ 351/210
    See application file for complete search history.

(56) References Cited

U.S. PATENT DOCUMENTS

| | | |
|---|---|---|
| 2013/0194545 A1 | 8/2013 | Ono |
| 2013/0293837 A1 | 11/2013 | Akiba |
| 2014/0375952 A1* | 12/2014 | Hanebuchi ............ A61B 3/103 |
| | | 351/206 |
| 2018/0125359 A1 | 5/2018 | Doble et al. |
| 2019/0008378 A1 | 1/2019 | Hayashi et al. |

FOREIGN PATENT DOCUMENTS

| | | |
|---|---|---|
| JP | 2017-136215 A | 8/2017 |
| WO | 2016/176415 A1 | 11/2016 |

OTHER PUBLICATIONS

Office Action dated Jul. 5, 2021, in corresponding Chinese patent Application No. 201910628307.9, 14 pages.

* cited by examiner

OPHTHALMOLOGIC APPARATUS AND METHOD OF CONTROLLING THE SAME

CROSS-REFERENCE TO RELATED APPLICATION

This application is based upon and claims the benefit of priority from Japanese Patent Application No. 2018-150530, filed Aug. 9, 2018; the entire contents of which are incorporated herein by reference.

FIELD

Embodiments according to present invention described herein relate to an ophthalmologic apparatus and a method of controlling the same.

BACKGROUND

Ophthalmologic apparatuses capable of performing a plurality of inspections and measurements for a subject's eye are known. The inspections and the measurements for the subject's eye include a subjective inspection and an objective measurement. The subjective inspection is to acquire the result based on the responses from the subject. The objective measurement is to acquire information on the subject's eye mainly by the use of a physical method without referring to the responses from the subject.

For example, Japanese Unexamined Patent Application Publication No. 2017-136215 discloses an ophthalmologic apparatus capable of performing the subjective inspection and the objective measurement. In this ophthalmologic apparatus, the refractive power measurement of the subject's eye, the photographing using optical coherence tomography, and the measurement using optical coherence tomography can be performed as the objective measurement.

SUMMARY

One aspect of some embodiments is an ophthalmologic apparatus comprising: a refractometry optical system configured to project light onto a subject's eye and to detect returning light from the subject's eye; an OCT optical system configured to split light from an OCT light source into measurement light and reference light, to project the measurement light onto the subject's eye, and to detect interference light between returning light of the measurement light from the subject's eye and the reference light; a fixation projection system configured to simultaneously project a first fixation target and a second fixation target onto the subject's eye, a visual angle of the second fixation target being narrower than a visual angle of the first fixation target; and a controller configured to control the refractometry optical system and the OCT optical system to simultaneously perform a refractometry and an OCT measurement.

Another aspect of some embodiments is a method of controlling an ophthalmologic apparatus, the ophthalmologic apparatus comprising: a refractometry optical system configured to project light onto a subject's eye and to detect returning light from the subject's eye; an OCT optical system configured to split light from an OCT light source into measurement light and reference light, to project the measurement light onto the subject's eye, and to detect interference light between returning light of the measurement light from the subject's eye and the reference light; a fixation projection system configured to project a first fixation target and a second fixation target onto the subject's eye, a visual angle of the second fixation target being narrower than a visual angle of the first fixation target; and a controller, the method comprising: a projection step that controls the fixation projection system to simultaneously project the first fixation target and the second fixation target onto the subject's eye; and a measurement step that controls the refractometry optical system and the OCT optical system to simultaneously perform a refractometry and an OCT measurement while simultaneously projecting the first fixation target and the second fixation target onto the subject's eye.

DETAILED DESCRIPTION

Figure 1:
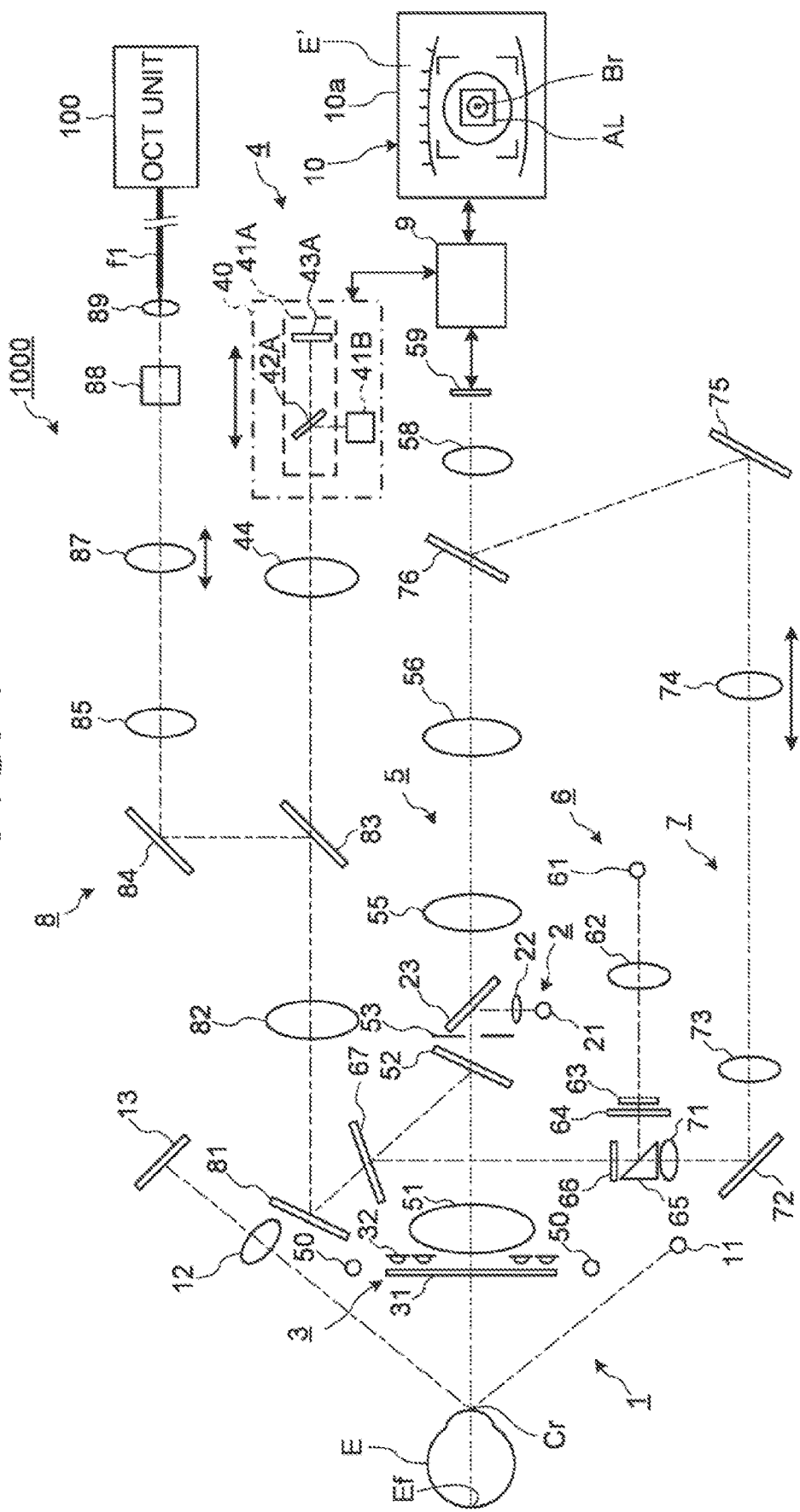
FIG. 1 is a schematic diagram illustrating an example of a configuration of an optical system of an ophthalmologic apparatus according to the first embodiment.

In the conventional ophthalmologic apparatuses, a plurality of inspections and the like can be performed. However, each of the inspections and the like is sequentially performed. For example, in the ophthalmologic apparatus capable of performing refractive power measurement and OCT measurement, the time for inspection becomes long and it becomes a burden on a subject, since each of the measurements and the like is sequentially performed.

According to some embodiments of the present invention, an ophthalmologic apparatus and a method of controlling the same, which can shorten the time for measurement and the like in the ophthalmologic apparatus capable of performing refractive power measurement and OCT measurement, can be provided.

Referring now to the drawings, exemplary embodiments of an ophthalmologic apparatus and a method of controlling the ophthalmologic apparatus according to the present invention are described below. Any of the contents of the documents cited in the present specification and arbitrary known techniques may be applied to the embodiments below.

In an ophthalmologic apparatus according to the embodiments, a refractive power measurement, a measurement using optical coherence tomography (hereinafter referred to as OCT), and a photographing using OCT can be performed.

Hereinafter, the case of using the method of swept source type OCT in the measurement using OCT or the like will be described in detail in the embodiments. However, the configuration according to the embodiments can be applied to ophthalmologic apparatuses using another type OCT (for example, the spectral domain type).

An ophthalmologic apparatus according to some embodiments further includes a subjective inspection optical system for performing subjective inspection and an objective measurement system for performing other objective measurement.

The subjective inspection is a method for measurement to acquire information using the responses from the subject. Examples of the subjective inspection include a visual field test, and a subjective refractometry such as a far vision test, a near vision test, a contrast test, a glare test or the like.

The objective measurement is a method for measurement to acquire information on a subject's eye mainly by the use of a physical method without referring to the responses from the subject. The objective measurements include a measurement for acquiring the characteristics of the subject's eye and a photographing for acquiring an image of the subject's eye. Examples of the other objective measurements include a keratometry, a tonometry, a fundus photography, and the like.

Hereinafter, a fundus conjugate position is a position substantially optically conjugate with a fundus of the subject's eye in a state where alignment is completed, and means a position optically conjugate with the fundus of the subject's eye or the vicinity of the position. Similarly, a pupil conjugate position is a position substantially optically conjugate with a pupil of the subject's eye in a state where alignment is completed, and means a position optically conjugate with the pupil of the subject's eye or the vicinity of the position.

First Embodiment

An ophthalmologic apparatus according to the first embodiment includes a plurality of optical systems for performing a plurality of inspections and measurements. The ophthalmologic apparatus is capable of simultaneously performing the inspections etc. while simultaneously presenting fixation targets for performing the inspections etc. In the first embodiment, an objective lens common to the optical systems is provided and the inspections etc. are performed using light having different wavelength ranges each other. Hereinafter, the ophthalmologic apparatus capable of simultaneously performing refractometry and OCT measurement among the objective measurements will be described. However, the embodiments described after can be applied to combinations other than the refractometry and the OCT measurement.

<Configuration of Optical System>

FIG. 1 illustrates an example of the configuration of an optical system of the ophthalmologic apparatus according to the first embodiment. The ophthalmologic apparatus 1000 according to the first embodiment includes an optical system for observing the subject's eye E, an optical system for inspecting the subject's eye E, and a dichroic mirror that wavelength-separates the optical paths of these optical systems. An anterior segment observation (imaging) system 5 is provided as the optical system for observing the subject's eye E. An OCT optical system, a refractometry optical system (refractive power measurement optical system), and the like are provided as the optical system for inspecting the subject's eye E.

The ophthalmologic apparatus 1000 includes a Z alignment system 1, a XY alignment system 2, a keratometry system 3, a fixation projection system 4, the anterior segment observation system 5, a refractometry projection system 6, a refractometry light reception system 7, and an OCT optical system 8. Hereinafter, for example, it is assumed that light with 940 nm to 1000 nm is used in the anterior segment observation system 5, light with 830 nm to 880 nm is used in the refractometry optical system (refractometry projection system 6, refractometry light reception system 7), light with 400 nm to 700 nm is used in the fixation projection system 4, and light with 1000 nm to 1100 nm is used in the OCT optical system 8.

It should be noted that light in a wavelength range including 780 nm may be used in the refractometry optical system and light in a wavelength range including 860 nm may be used in the OCT optical system 8. In this case, for example, light with 940 nm to 1000 nm can be used in the anterior segment observation system 5, light with 760 nm to 800 nm can be used in the refractometry optical system, light with 400 nm to 700 nm can be used in the fixation projection system 4, and light with 810 nm to 860 nm can be used in the OCT optical system 8.

(Anterior Segment Observation System 5)

The anterior segment observation system 5 is configured to acquire a moving image of an anterior segment of the subject's eye E. In an optical system passing through the anterior segment observation system 5, an imaging plane of an imaging element 59 is arranged at the pupil conjugate position. An anterior segment illumination light source 50 irradiates illumination light (for example, infrared light) on the anterior segment of the subject's eye E. Light reflected from the anterior segment of the subject's eye E passes through an objective lens 51, is transmitted through a dichroic mirror 52, passes through an aperture part formed in a diaphragm (telecentric diaphragm) 53, is transmitted through a half mirror 23, passes through relay lenses 55 and 56, and is transmitted through a dichroic mirror 76. The dichroic mirror 52 combines (or separates) the optical path of the refractometry optical system with the optical path of the anterior segment observation system 5. The dichroic mirror 52 is disposed so that its optical path combining surface for combining these optical paths is inclined with respect to an optical axis of the objective lens 51. Light transmitted through the dichroic mirror 76 forms an image on the imaging surface of the imaging element 59 (area sensor) by an imaging lens 58. The imaging element 59 performs an imaging and a signal outputting at a predetermined rate. The output (video signal) of the imaging element 59 is input to a processing unit (processor) 9 described after. The processing unit 9 displays an anterior segment image E' based on this video signal on a display screen 10a of a display unit 10 described after. The anterior segment image E' is an infrared moving image for example.

(Z Alignment System 1)

The Z alignment system 1 is configured to project light (infrared light) for performing alignment in an optical axis direction (front-back directions, Z direction) of the anterior segment observation system 5 onto the subject's eye E. Light emitted from a Z alignment light source 11 is projected onto a cornea Cr of the subject's eye E, is reflected by the cornea Cr, and forms an image on a sensor surface of a line sensor 13 by an imaging lens 12. When the position of a corneal apex changes in the optical axis direction of the anterior segment observation system 5, the projection position of the light onto the sensor surface of the line sensor 13 changes. The processing unit 9 obtains a position of the corneal apex of the subject's eye E based on the projection position of the light onto the sensor surface of the line sensor 13 and controls a mechanism for moving the optical system to perform Z alignment based on this.

(XY Alignment System 2)

The XY alignment system 2 is configured to project light (infrared light) for performing alignment in a direction (left-right directions (X direction), up-down directions (Y direction)) orthogonal to the optical axis direction of the anterior segment observation system 5 onto the subject's eye E. The XY alignment system 2 includes a XY alignment light source 21 and a collimator lens 22 that are provided in an optical path branched from the optical path of the anterior segment observation system 5 by the half mirror 23. The light emitted from the XY alignment light source 21 passes through the collimator lens 22, is reflected by the half mirror 23, and is projected onto the subject's eye E through the anterior segment observation system 5. Reflected light from the cornea Cr of the subject's eye E is guided to the imaging element 59 through the anterior segment observation system 5.

An image (bright spot image) Br based on the reflected light is included in the anterior segment image E'. The processing unit 9 controls the display unit to display an alignment mark AL and the anterior segment image E' including the bright spot image Br on the display screen of the display unit. In the case of performing XY alignment manually, a user can perform an operation for moving the optical system so as to guide the bright spot image Br in the alignment mark AL. In the case of performing XY alignment automatically, the processing unit 9 controls a mechanism for moving the optical system so as to cancel a displacement of the bright spot image Br with respect to the alignment mark AL.

(Keratometry System 3)

The keratometry system 3 is configured to project a ring-shaped light flux (infrared light) for measuring a shape of the cornea Cr of the subject's eye E onto the cornea Cr. A kerato plate (keratometry plate) 31 is disposed between the objective lens 51 and the subject's eye E. A kerato-ring light source (keratometry ring light source, keratometry light source) 32 is provided on the back side (objective lens 51 side) of the kerato plate 31. In the kerato plate 31, a kerato (keratometry) pattern (transmitting part, light transmitting part) that transmits light from the kerato-ring light source 32 is formed along a circumference around the optical axis of the objective lens 51. It should be noted that the kerato pattern may be formed in an arc shape (a part of the circumference) around the optical axis of the objective lens 51. By illuminating the kerato plate 31 with light from the kerato-ring light source 32, the ring-shaped light flux (arc-like or circumferential (circular) measurement pattern) is projected onto the cornea Cr. The reflected light (kerato-ring image) from the cornea Cr of the subject's eye E is detected by the imaging element 59 along with the anterior segment image E'. The processing unit 9 calculates a corneal shape parameter representing a shape of the cornea Cr, by performing a known calculation based on this kerato-ring image.

(Refractometry Projection System 6 and Refractometry Light Reception System 7)

The refractometry optical system includes the refractometry projection system 6 and the refractometry light reception system 7 which are used for refractive power measurement. The refractometry projection system 6 is configured to project light flux (a ring-shaped light flux, for example) (infrared light) for measuring refractive power onto the fundus Ef. The refractometry light reception system 7 is configured to receive returning light of the light flux from the subject's eye E. The refractometry projection system 6 is provided in an optical path branched by a perforated prism 65 provided in an optical path of the refractometry light reception system 7. A hole part formed in the perforated prism 65 is arranged at the pupil conjugate position. In an optical system passing through the refractometry light reception system 7, the imaging surface of the imaging element 59 is arranged at the fundus conjugate position.

In some embodiments, the refractometry light source 61 is a SLD (Super Luminescent Diode) light source which is a high-intensity light source. The refractometry light source 61 is movable in an optical axis direction. The refractometry light source 61 is arranged at the fundus conjugate position. Light emitted from the refractometry light source 61 passes through the relay lens 62 and is incident on a conical surface of the conical prism 63. The light incident on the conical surface is deflected and emits from a bottom surface of the conical prism 63. The light emitted from the bottom surface of the conical prism 63 passes through a ring-shaped light transmission part formed in a ring diaphragm 64. The light (ring-shaped light flux) passing through the light transmission part of the ring diaphragm 64 is reflected on a reflective surface formed around the hole part of the perforated prism 65, passes through a rotary prism 66, and is reflected by the dichroic mirror 67. The light reflected by the dichroic mirror 67 is reflected by the dichroic mirror 52, passes through the objective lens 51, and is projected onto the fundus Ef. The rotary prism 66 is used for averaging the light quantity distribution of the ring-shaped light flux with respect to the blood vessel or the diseased site of the fundus Ef or for reducing the speckle noise caused by the light source.

Returning light of the ring-shaped light flux projected onto the fundus Ef passes through the objective lens 51, and is reflected by the dichroic mirrors 52 and 67. The returning light reflected by the dichroic mirror 67 passes through the rotary prism 66, passes through the hole part of the perforated prism 65, passes through a relay lens 71, is reflected by a reflective mirror 72, and passes through a relay lens 73 and a focusing lens 74. The focusing lens 74 is movable along an optical axis of the refractometry light reception system 7. The light passing through the focusing lens 74 is reflected by the reflective mirror 75, is reflected by the dichroic mirror 76, and forms an image on the imaging surface of the imaging element 59 by the imaging lens 58. The processing unit 9 calculates a refractive power value of the subject's eye E by performing the known calculation based on the output of the imaging element 59. For example, refractive power value includes a spherical power, a degree of astigmatism, and an astigmatic axis angle, or an equivalent spherical power.

(Fixation Projection System 4)

The OCT optical system 8, which will be described after, is provided in the optical path wavelength-separated from the optical path of the refractometry optical system by the dichroic mirror 67. The fixation projection system 4 is provided in the optical path branched from the optical path of the OCT optical system 8 by the dichroic mirror 83.

The fixation projection system 4 is configured to present a fixation target to the subject's eye E. The fixation projection system 4 can simultaneously present a fixation target (optotype) for refractometry and a fixation target for OCT measurement to the subject's eye E. A fixation unit 40 is disposed in the optical path of the fixation projection system 4. The fixation unit 40 is movable along an optical axis of the fixation projection system 4 under the control of the processing unit 9 described after. A relay lens 44 is arranged between the dichroic mirror 83 ant the fixation unit 40.

The fixation unit 40 includes a first fixation target projection system 41A, a second fixation target projection system 41B, and a half mirror 42A. The first fixation target projection system 41A is configured to project a fixation target for refractometry onto the subject's eye E. The second fixation target projection system 41B is configured to project a fixation target for OCT measurement onto the subject's eye E. The half mirror 42A combines an optical path of the second fixation target projection system 41B with an optical path of the first fixation target projection system 41A.

In refractometry, for the purpose of measuring the refractive power of the subject's eye under far vision, the fixation target is presented to the subject's eye E so as not to accommodate (adjust visual acuity). Specially, in the refractometry, the fixation targets with a large visual angle are used, which allows the subject's eye E to be viewed as far as possible, and to reduce the influence of the instrument myopia. For example, a landscape chart or the like is used as such a fixation target for refractometry. The first fixation target projection system 41A includes a visual target chart 43A on which the fixation target for refractometry is displayed. For example, the visual target chart 43A is a transmissive type. Light from an illumination light source provided on the back side is irradiated on the visual target chart 43A. In some embodiments, a liquid crystal panel capable of displaying a pattern representing a fixation target for refractometry under the control of the processing unit 9 is provided instead of the visual target chart 43A.

When the refractometry is performed, the visual target chart 43A is disposed at a position where a fogging of the subject's eye E is promoted, by moving the fixation unit 40 along the optical path of the fixation projection system 4.

In OCT measurement, the fixation target is presented to the subject's eye E so that a desired site of the subject's eye E is arranged at a predetermined measurement position according to the site to be measured or the purpose of the measurement. Specifically, in the OCT measurement, the fixation targets with a small visual angle are used, which allows the subject's eye E to continue fixation in a desired direction for a predetermined time. For example, a bright spot (dot visual target), cross visual target, or the like is used as such a fixation target for OCT measurement. That is, the visual angle of the fixation target for OCT measurement is narrower than the visual angle of the fixation target for refractometry. The second fixation target projection system 41B includes a fixation light source (point light source) for projecting a bright spot for OCT measurement. In some embodiments, a liquid crystal panel capable of displaying a pattern representing a fixation target for OCT measurement under the control of the processing unit 9 is provided instead of the fixation light source.

When the OCT measurement is performed, the fixation light source is disposed at the fundus conjugate position independently of the first fixation target projection system 41A. In some embodiments, the fixation light source is moved along the optical path of the second fixation target projection system 41B. In some embodiments, a lens arranged between the half mirror 42A and the fixation light source is moved along the optical path of the second fixation target projection system 41B. In case that the spot size of the bright spot projected onto the subject's eye E by the fixation light source is sufficiently small, the fixation light source may be moved integrally with the first fixation target projection system 41A.

In case that the liquid crystal panel displaying the patter representing the fixation target is used, the fixation position of the subject's eye E can be changed by changing the display position of the fixation target on the screen of the liquid crystal panel under the control of the processing unit 9. Examples of the fixation position of the subject's eye E include a position for acquiring an image centered at a macular region of the fundus Ef, a position for acquiring an image centered at an optic disc, and a position for acquiring an image centered at the fundus center between the macular region and the optic disc. The display position of the pattern representing the fixation target can be arbitrarily changed.

Light (fixation light flux) for projecting the fixation target for refractometry from the first fixation target projection system 41A and light for projecting the fixation target for OCT measurement from the second fixation target projection system 41B are combined by the half mirror 42A. The combined light by the half mirror 42A passes through the relay lens 44, is transmitted through the dichroic mirror 83, passes through a relay lens 82, is reflected by a reflective mirror 81, is passed through the dichroic mirror 67, and is reflected by the dichroic mirror 52. The light reflected by the dichroic mirror 52 passes through the objective lens 51 and is projected onto a fundus Ef.

(OCT Optical System 8)

The OCT optical system 8 is an optical system for performing OCT measurement. The position of the focusing lens 87 is adjusted so that an end face of an optical fiber f1 and a photographing site (fundus Ef or the anterior segment) are optically conjugate with each other based on the result of the refractometry performed before the OCT measurement.

The OCT optical system 8 is provided in the optical path wavelength-separated from the optical path of the refractometry optical system by the dichroic mirror 67. The optical path of the above fixation projection system 4 is coupled with the optical path of the OCT optical system 8 by the dichroic mirror 83. Thereby, the optical axes of the OCT optical system 8 and the fixation projection system 4 can be coupled coaxially.

Figure 2:
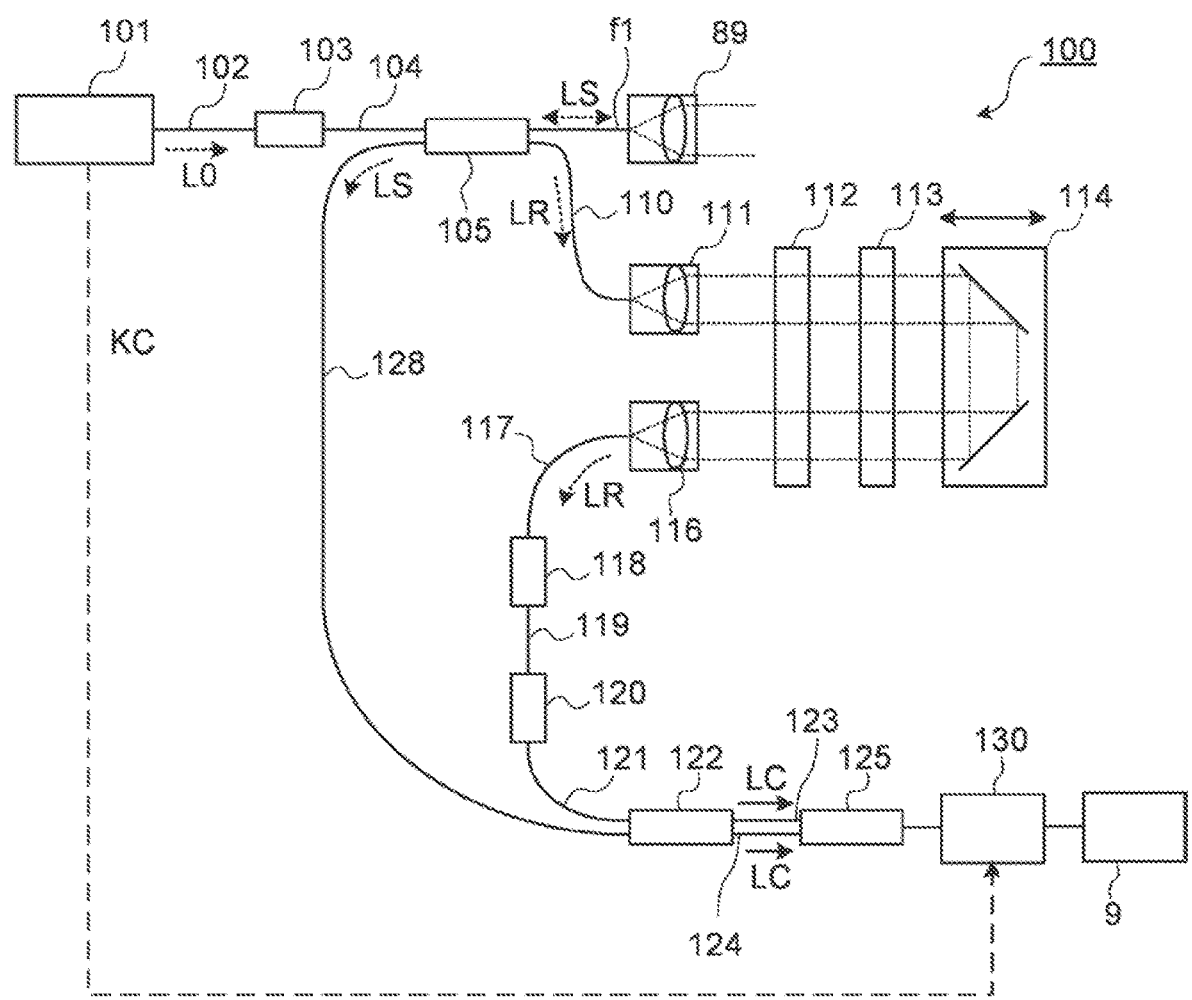
FIG. 2 is a schematic diagram illustrating an example of a configuration of the optical system of the ophthalmologic apparatus according to the first embodiment.

The OCT optical system 8 includes an OCT unit 100. As illustrated in FIG. 2, in the OCT unit 100, like general swept-source-type OCT apparatuses, an OCT light source 101 includes a wavelength tunable type (a wavelength scanning type) light source capable of sweeping (scanning) the wavelengths of emitted light. The wavelength tunable type light source includes a laser light source that includes a resonator. The OCT light source 101 temporally changes the output wavelength in the near infrared wavelength band which cannot be visually recognized by the human eye.

As illustrated by an example in FIG. 2, the OCT unit 100 is provided with an optical system for performing swept source OCT. This optical system includes an interference optical system. This interference optical system has a function that splits light from the wavelength tunable type (wavelength scanning type) light source into measurement light and reference light, a function that makes the returning light of the measurement light from the subject's eye E and the reference light having traveled through a reference optical path interfere with each other and generates interference light, and a function that detects the interference light. The detection result (detection signal, interference signal) of the interference light obtained by the interference optical system is a signal indicating a spectrum of the interference light, and is sent to the processing unit 9.

The OCT light source 101 includes a near-infrared tunable laser which changes the wavelength of the emitted light at high speed, for example. Light L0 output from the OCT light source 101 is guided to the polarization controller 103 through the optical fiber 102, and the polarization state of the light L0 is adjusted. The light L0 whose polarization state has been adjusted is guided to the fiber coupler 105 through the optical fiber 104. The fiber coupler 105 splits the light L0 into the measurement light LS and the reference light LR.

The reference light LR is guided to the collimator 111 through the optical fiber 110. The reference light LR is converted into a parallel light beam by the collimator 111. Then, the reference light LR is guided to the corner cube 114 via an optical path length correction member 112 and a dispersion compensation member 113. The optical path length correction member 112 acts so as to match the optical path length of the reference light LR with the optical path length of the measurement light LS. The dispersion compensation member 113 acts so as to match the dispersion characteristics between the reference light LR and the measurement light LS. The corner cube 114 is movable in the incident direction of the reference light LR. With this, the length of the optical path of the reference light LR is changed.

The reference light LR that has traveled through the corner cube 114 passes through the dispersion compensation member 113 and the optical path length correction member 112, is converted from the parallel light beam to the convergent light beam by a collimator 116, and enters an optical fiber 117. The reference light LR that has entered the optical fiber 117 is guided to a polarization controller 118, and the polarization state of the reference light LR is adjusted. Then the reference light LR is guided to an attenuator 120 through an optical fiber 119, and the light amount of the reference light LR is adjusted. After that, the reference light LR is guided to a fiber coupler 122 through an optical fiber 121.

Meanwhile, the measurement light LS generated by the fiber coupler 105 is guided through the optical fiber f1, is made into the parallel light beam by the collimator lens unit 89, is reflected by the dichroic mirror 83 via an optical scanner 88, the focusing lens 87, a relay lens 85, and a reflective mirror 84.

The optical scanner 88 deflects the measurement light LS in a one-dimensionally or two-dimensional manner. The optical scanner 88 includes a first galvano mirror and a second galvano mirror, for example. The first galvano mirror deflects the measurement light LS so as to scan the photographing site (fundus Ef or the anterior segment) in a horizontal direction orthogonal to the optical axis of the OCT optical system 8. The second galvano mirror deflects the measurement light LS deflected by the first galvano mirror so as to scan the photographing site in a vertical direction orthogonal to the optical axis of the OCT optical system 8. Examples of scan modes with the measurement light LS performed by the optical scanner 88 like this include horizontal scan, vertical scan, cross scan, radial scan, circle scan, concentric scan, helical (spiral) scan, and the like.

The measurement light LS reflected by the dichroic mirror 83 passes through the relay lens 82, is reflected by the reflective mirror 81, is transmitted through the dichroic mirror 67, is reflected by the dichroic mirror 52, is refracted by the objective lens 51, and is incident on the subject's eye E. The measurement light LS is scattered and reflected at various depth positions of the subject's eye E. The returning light of the measurement light LS from the subject's eye E advances in the same path as the forward path in the opposite direction, is guided to the fiber coupler 105, and then reaches the fiber coupler 122 via the optical fiber 128.

The fiber coupler 122 combines (interferes) the measurement light LS incident through the optical fiber 128 and the reference light LR incident through the optical fiber 121 to generate interference light. The fiber coupler 122 splits the interference light at a predetermined splitting ratio (e.g., 1:1) to generate a pair of interference light LC. The pair of interference light LC is guided to a detector 125 through optical fibers 123 and 124, respectively.

The detector 125 is a balanced photodiode, for example. The balanced photodiode includes a pair of photodetectors that respectively detect the pair of interference light LC and output the difference between a pair of detection results acquired by the pair of photodetectors. The detector 125 sends the output (detection signal) to a DAQ (data acquisition system) 130.

The DAQ 130 is fed with a clock KC from the OCT light source 101. The clock KC is generated in the OCT light source 101 in synchronization with the output timing of each wavelength within a predetermined wavelength range performed by the wavelength tunable type light source. For example, the OCT light source 101 optically delays one of the two pieces of branched light obtained by branching the light L0 of each output wavelength, and then generates the clock KC based on the result of the detection of the combined light of the two pieces of branched light. The DAQ 130 performs sampling the detection signal input from the detector 125 based on the clock KC. The DAQ 130 sends the result of sampling the detection signal from the detector 125 to an arithmetic processor 220 of the processing unit 9. For example, the arithmetic processor 220 performs the Fourier transform, etc. on the spectral distribution based on the sampling data for each series of wavelength scanning (i.e., for each A line). With this, the reflection intensity profile for each A line is formed. In addition, the arithmetic processor 220 forms image data by applying imaging processing to the reflection intensity profiles of the respective A lines.

In the present example, the corner cube 114 is provided for changing the length of the optical path of the reference light LR (reference optical path, reference arm); however, the difference between the measurement optical path length and the reference optical path length may be changed using another kind of optical member.

The processing unit 9 calculates the refractive power value from the result of the measurement obtained using the refractometry optical system, and controls the refractometry light source 61 and the focusing lens 74 to move respectively to positions where the fundus Ef, the refractometry light source 61, and the imaging element 59 are conjugate with each other, in the optical axis direction based on the calculated refractive power value. In some embodiments, the processing unit 9 controls the focusing lens 87 of the OCT optical system 8 to move in its optical axis direction in conjunction with the movement of the focusing lens 74. In some embodiments, the processing unit 9 controls the fixation unit 40 to move in its optical axis direction in conjunction with the movement of the refractometry light source 61 and the focusing lens 74.

<Configuration of Processing System>

Figure 3:
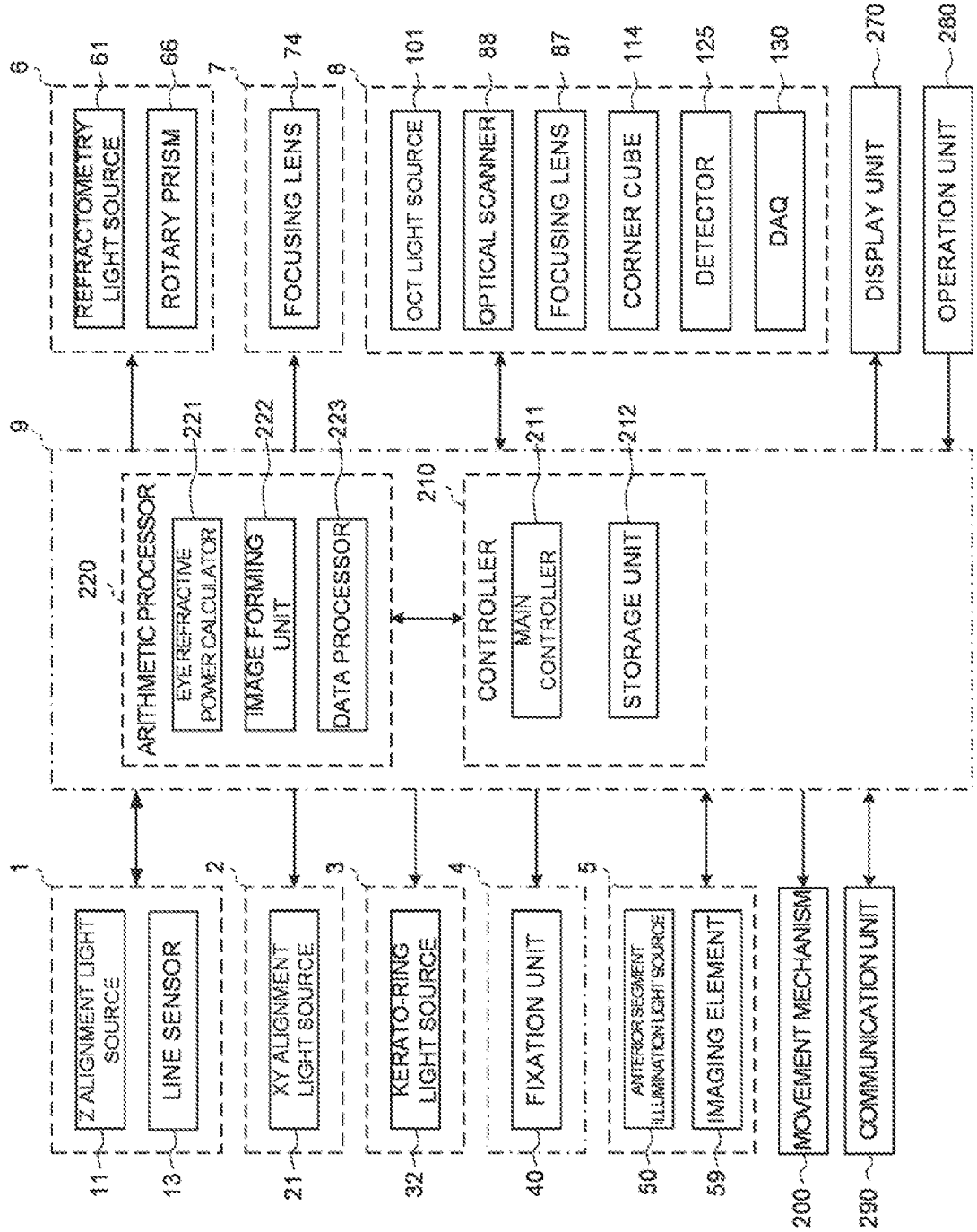
FIG. 3 is a schematic diagram for explaining a processing system of the ophthalmologic apparatus of the first embodiment.

The processing system of the ophthalmologic apparatus 1000 will be described. FIG. 3 illustrates an example of the functional structure of the processing system of the ophthalmologic apparatus 1000. FIG. 3 shows an example of a functional block diagram illustrating the processing system of the ophthalmologic apparatus 1000.

The processing unit 9 controls each part of the ophthalmologic apparatus 1000. Further, the processing unit 9 is capable of performing various types of arithmetic processing. The processing unit 9 includes a processor. The function of the processor is implemented by a circuit(s) such as, for example, a CPU (central processing unit), a GPU (graphics processing unit), an ASIC (application specific integrated circuit), and a PLD (programmable logic device). Examples of PLD include a simple programmable logic device (SPLD), a complex programmable logic device (CPLD), and a field programmable gate array (FPGA). The processing unit 9 realizes the function according to the embodiments, for example, by reading out a computer program stored in a storage circuit or a storage device and executing the computer program.

The processing unit 9 includes a controller 210 and the arithmetic processor 220. Further, the ophthalmologic apparatus 1000 includes a movement mechanism 200, a display unit 270, an operation unit 280, and a communication unit 290.

The movement mechanism 200 is a mechanism for moving a head unit in front, back, left and right directions, the head unit housing the optical systems such as the Z alignment system 1, the XY alignment system 2, the keratometry system 3, the fixation projection system 4, the anterior segment observation system 5, the refractometry projection system 6, the refractometry light reception system 7, the OCT optical system 8, and the like. For example, the movement mechanism 200 is provided with an actuator that generates driving force for moving the head unit and a transmission mechanism that transmits the driving force to the head unit. The actuator is configured by a pulse motor, for example. The transmission mechanism is configured by a combination of gears, a rack and pinion, and the like, for example. The controller 210 (main controller 211) controls the movement mechanism 200 by sending a control signal to the actuator.

(Controller 210)

The controller 210 includes a processor and controls each part of the ophthalmologic apparatus. The controller 210 includes the main controller 211 and a storage unit 212. The storage unit 212 stores, in advance, a computer program for controlling the ophthalmologic apparatus. The computer program includes programs for controlling light source, programs for controlling detector, programs for controlling optical scanner, programs for controlling optical system, programs for arithmetic processing, programs for user interface, and the like. The main controller 211 operates according to the computer programs, and thereby the controller 210 performs the control processing.

The main controller 211 performs various controls of the ophthalmologic apparatus, as a measurement controller. Examples of control for the Z alignment system 1 include control of the Z alignment light source 11, control of the line sensor 13, and the like. Examples of the control of the Z alignment light source 11 include turning on and off of the light source, adjustment of an amount of light, adjustment of aperture, and the like. Examples of the control of the line sensor 13 include adjustment of exposure of a detecting element, adjustment of gain of the detecting element, adjustment of detecting rate of the detecting element, and the like. Thereby, the Z alignment light source 11 can be switched between lighting and non-lighting or the amount of light can be changed. The main controller 211 acquires a signal detected by the line sensor 13 and specifies the projection position of light onto the line sensor 13 based on the acquired signal. The main controller 211 specifies a position of a corneal apex of the subject's eye E based on the specified projection position and controls the movement mechanism 200 based on the specified position to move the head unit in front and back directions (Z alignment).

Examples of control for the XY alignment system 2 include control of the XY alignment light source 21, and the like. Examples of the control of the XY alignment light source 21 include turning on and off of the light source, adjustment of an amount of light, adjustment of aperture, and the like. Thereby, the XY alignment light source 21 can be switched between lighting and non-lighting, or the amount of light can be changed. The main controller 211 acquires a signal detected by the imaging element 59, and specifies a position of a bright spot image on the basis of returning light of the light from the XY alignment light source 21 based on the acquired signal. The main controller 211 controls the movement mechanism 200 to move the head unit in left, right, up, down directions so as to cancel a displacement the position of the bright spot image with respect to a predetermined target position (for example, a center position of the alignment mark AL) (XY alignment).

Examples of control for the keratometry system 3 include control of the kerato-ring light source 32, and the like. Examples of the control of the kerato-ring light source 32 include turning on and off of the light source, adjustment of an amount of light, adjustment of aperture, and the like. Thereby, the kerato-ring light source 32 can be switched between lighting and non-lighting, or the amount of light can be changed. The main controller 211 controls the arithmetic processor 220 to perform a known calculation on a kerato-ring image detected by the imaging element 59. Thereby, corneal shape parameters of the subject's eye E are obtained.

Examples of control for the fixation projection system 4 include control of the fixation unit 40, and the like. Examples of the control of the fixation unit 40 include movement control for the fixation unit 40, control for the first fixation target projection system 41A, control for the second fixation target projection system 41B, and the like.

The fixation projection system 4 includes a movement mechanism that moves the fixation unit 40 in the optical axis direction. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move the fixation unit 40 in the optical axis direction. Thereby, for example, after a position of the visual target chart 43A is adjusted so that the visual target chart 43A and the fundus Ef are optically conjugate with each other, the visual target chart 43A can be arranged at a position where a fogging of the subject's eye E is promoted by moving the visual target chart 43A by a predetermined shift (diopter). In addition, the fixation light source included in the second fixation target projection system 41B is similarly moved independently of the visual target chart 43A under the control of the main controller 211.

Examples of the control for the first fixation target projection system 41A include turning on and off of an illumination light source the visual target chart, change of an amount of light, and the like. In the case that the first fixation target projection system 41A includes a liquid crystal panel, examples of the control for the first fixation target projection system 41A include displaying on and off the fixation target, switching patterns representing the fixation targets according to the type of the inspection or the measurement, switching the display position of the pattern representing the fixation target, and the like. Examples of the control for the second fixation target projection system 41B include turning on and off a light source for projecting the bright spot, change of an amount of light, and the like. In the case that the second fixation target projection system 41B includes a liquid crystal panel, examples of the control for the second fixation target projection system 41B include displaying on and off the fixation target, switching patterns representing the fixation targets according to the type of the inspection or the measurement, switching the display position of the pattern representing the fixation target, and the like.

Figure 4A:
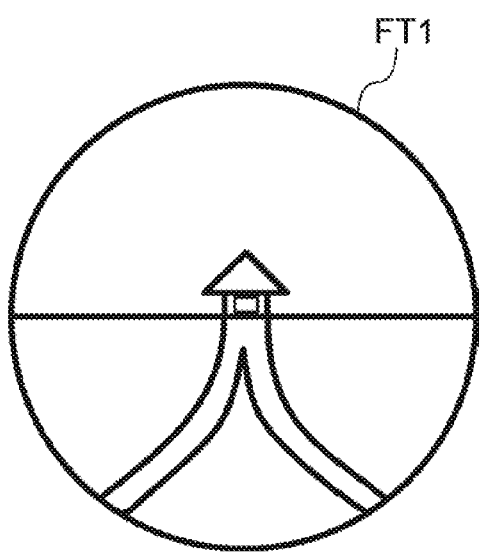
FIG. 4A is a schematic diagram for explaining the ophthalmologic apparatus of the first embodiment.
Figure 4B:
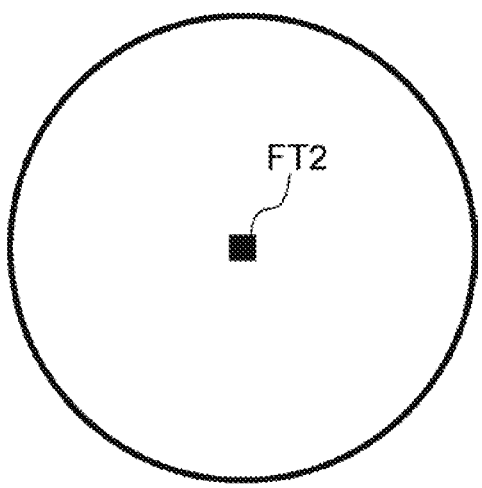
FIG. 4B is a schematic diagram for explaining the ophthalmologic apparatus of the first embodiment.
Figure 4C:
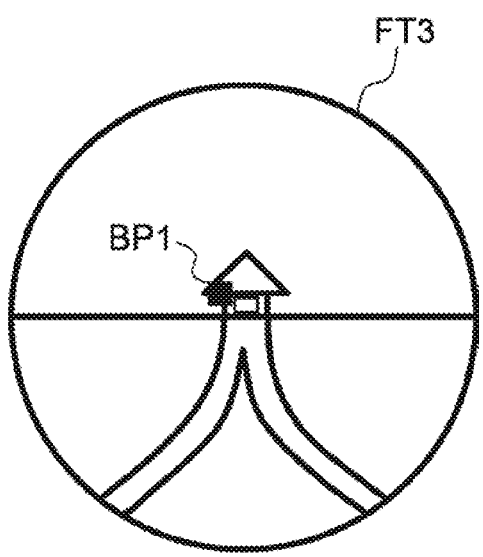
FIG. 4C is a schematic diagram for explaining the ophthalmologic apparatus of the first embodiment.

FIGS. 4A to 4C show explanatory diagrams of the fixation target(s) projected onto the subject's eye E by the fixation projection system 4 according to the first embodiment. FIG. 4A shows explanatory diagram of the fixation target for refractometry projected onto the subject's eye E by the first fixation target projection system 41A. FIG. 4B shows explanatory diagram of the fixation target for OCT measurement projected onto the subject's eye E by the second fixation target projection system 41B. FIG. 4C shows explanatory diagram of the fixation target presented to the subject's eye E in which the refractometry and the OCT measurement are simultaneously performed.

The main controller 211 can control the refractometry optical system and the OCT optical system 8 to simultaneously perform the refractometry and the OCT measurement on the subject's eye E. At this time, the main controller 211 controls the first fixation target projection system 41A to project a fixation target FT1 shown in FIG. 4A onto the subject's eye E from a position where the fogging of the subject's eye E is promoted, and controls the second fixation target projection system 41B to project a fixation target FT2 shown in FIG. 4B onto the subject's eye E from the fundus conjugate position. The fixation target FT1 is a landscape chart. The fixation target FT2 is a bright spot (dot visual target) whose visual angle is smaller than that of the fixation target FT1. In some embodiments, the fixation target FT2 is a cross visual target whose visual angle is smaller than that of the fixation target FT1.

Therefore, a fixation target FT3 shown in FIG. 4C is presented to the subject's eye E in which the refractometry and the OCT measurement are simultaneously performed. The fixation target FT3 is a visual target in which a bright spot BP1 is superimposed on a predetermined position of the landscape chart. Thereby, the fixation target can be presented to the subject's eye E, on which the refractometry is performed, so as not to accommodate. And the fixation target can be presented to the subject's eye E, on which the OCT measurement is performed, so that a desired site of the subject's eye E is arranged at a predetermined measurement position.

In some embodiments, the main controller 211 controls the second fixation target projection system 41B to change the presentation state of the fixation target FT2. Examples of the change of the presentation state include blinking of the fixation target FT2 (bright spot BP1), temporal change of the luminance of the fixation target FT2, movement of the presentation position by the fixation target FT2, and the like.

As shown in FIG. 3, examples of the control for the anterior segment observation system 5 include control of the anterior segment illumination light source 50, control of the imaging element 59, and the like. Examples of control of the anterior segment illumination light source 50 include turning on and off the light source, adjustment of an amount of light, adjustment of aperture, and the like. Thereby, the anterior segment illumination light source 50 can be switched between lighting and non-lighting, or the amount of light can be changed. Example of the control of the imaging element 59 include adjustment of exposure of the imaging element 59, adjustment of gain of the imaging element 59, adjustment of detecting rate of the imaging element 59, and the like. The main controller 211 acquires a signal detected by the imaging element 59 and controls the arithmetic processor 220 to perform processing such as forming image based on the acquired signal and the like.

Examples of control for the refractometry projection system 6 include control of the refractometry light source 61, control of the rotary prism 66, and the like. Examples of the control of the refractometry light source 61 include turning on and off of the light source, adjustment of an amount of light, adjustment of aperture, and the like. Thereby, the refractometry light source 61 can be switched between lighting and non-lighting, or the amount of light can be changed. For example, the refractometry projection system 6 includes a movement mechanism that moves the refractometry light source 61 in the optical axis direction. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move the refractometry light source 61 in the optical axis direction. Examples of the control of the rotary prism 66 include control of rotating the rotary prism 66 and the like. For example, a rotary mechanism that rotates the rotary prism 66 is provided and the main controller 211 controls the rotary mechanism to rotate the rotary prism 66.

Examples of control for refractometry light reception system 7 include control of the focusing lens 74, and the like. Examples of the control of the focusing lens 74 include control of moving the focusing lens 74 in the optical axis direction. For example, the refractometry light reception system 7 include a movement mechanism that moves the focusing lens 74 in the optical axis direction. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move the focusing lens 74 in the optical axis direction. The main controller 211 is capable of moving the refractometry light source 61 and the focusing lens 74 in the optical axis direction respectively depending on the refractive power of the subject's eye E for example so that the refractometry light source 61 and the fundus Ef and the imaging element 59 are optically conjugate with each other.

Examples of control for the OCT optical system 8 include control of the OCT light source 101, control of the optical scanner 88, control of the focusing lens 87, control of the corner cube 114, control of the detector 125, control of the DAQ 130, and the like. Examples of the control of the OCT light source 101 includes turning on and off of the light source, adjustment of an amount of light, adjustment of aperture, and the like. Examples of the control of the optical scanner 88 include control of the scanning position and the scan range and the scanning speed by means of the first galvano mirror, control of the scanning position and the scan range and the scanning speed by means of the second galvano mirror, and the like.

Examples of the control of the focusing lens 87 include control of moving the focusing lens 87 in the optical axis direction, control of moving the focusing lens 87 to the in-focus reference position corresponding to the photographing site, control of moving the focusing lens 87 within the movement range (in-focus range) corresponding to the photographing site, and the like. For example, the OCT optical system 8 include a movement mechanism that moves the focusing lens 87 in the optical axis direction. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move the focusing lens 87 in the optical axis direction. In some embodiments, the ophthalmologic apparatus is provided with a holding member that holds the focusing lens 74 and the focusing lens 87, and the driver that drives the holding member. The main controller 211 controls the driver to move the focusing lenses 74 and 87. For example, the main controller 211 may moves the focusing lens 87 alone based on the intensity of the interference signal, after moving the focusing lens 87 in conjunction with the movement of the focusing lens 74.

Examples of the control of the corner cube 114 include control of moving the corner cube 114 along the optical path of the corner cube 114. For example, the OCT optical system 8 include a movement mechanism that moves the corner cube 114 along the optical path. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move the corner cube 114 along the optical path. Examples of the control of the detector 125 include adjustment of exposure of a detecting element, adjustment of gain of a detecting element, adjustment of detecting rate of a detecting element, and the like. The main controller 211 controls the DAQ 130 to perform sampling of the signal detected by the detector 125 and controls the arithmetic processor 220 (image forming unit 222) to perform processing such as forming image based on the sampled signal and the like.

Further, the main controller 211 performs a process of writing data in the storage unit 212 and a process of retrieving data from the storage unit 212.

(Storage Unit 212)

The storage unit 212 stores various types of data. Examples of the data stored in the storage unit 212 include a measurement result of the objective measurement, image data of a tomographic image, image data of a fundus image, subject's eye information, and the like. The subject's eye information includes information on the subject such as patient ID and name, and information on the subject's eye such as identification information of the left eye/right eye. The storage unit 212 further stores various types of programs and data to run the ophthalmologic apparatus.

(Arithmetic Processor 220)

The arithmetic processor 220 includes an eye refractive power calculator 221, the image forming unit 222, and a data processor 223.

The eye refractive power calculator 221 analyzes a ring image (pattern image) acquired by receiving the returning light of the ring-shaped light flux (ring-shaped measurement pattern) by the imaging element 59, the ring-shaped light flux being projected onto the fundus Ef by the refractometry projection system 6. For example, the eye refractive power calculator 221 obtains a position of the center of gravity of the ring image from the brightness distribution in the image representing the acquired ring image, obtains brightness distributions along a plurality of scanning directions extending radially from the position of the center of gravity, and specifies a ring image from this brightness distributions. Subsequently, the eye refractive power calculator 221 obtains an approximate ellipse of the specified ring image and obtains a spherical power, an astigmatic power, and an astigmatic axis angle by assigning a major axis and a minor axis of the approximate ellipse to a known formula. Alternatively, the eye refractive power calculator 221 can obtain the eye refractive power parameter based on deformation and displacement of the ring image with respect to the reference pattern.

Further, the eye refractive power calculator 221 calculates a corneal refractive power, a corneal astigmatism power, and a corneal astigmatic axis angle based on the kerato-ring image acquired by the anterior segment observation system 5. For example, the eye refractive power calculator 221 calculates a corneal curvature radius of the steepest meridian and/or the flattest meridian of the anterior surface of the cornea by analyzing the kerato-ring image and calculates above parameters based on the corneal curvature radius.

The image forming unit 222 forms image data of a tomographic image of the fundus Ef based on a signal detected by the detector 125. That is, the image forming unit 222 forms the image data of the subject's eye E based on a detection result of the interference light LC obtained by the interference optical system. Like the conventional spectral-domain-type OCT, this process includes processes such as filtering and FFT (Fast Fourier Transform). The image data acquired in this manner is a data set including a group of image data formed by imaging the reflection intensity profiles of a plurality of A lines. Here, the A lines are the paths of the measurement light LS in the subject's eye E.

In order to improve the image quality, it is possible to repeatedly perform scan with the same pattern a plurality of times to collect a plurality of data sets, and to compose (i.e., average) the plurality of data sets.

The data processor 223 performs various kinds of data processing (e.g., image processing) and various kinds of analysis on a tomographic image formed by the image forming unit 222. For example, the data processor 223 performs various correction processes such as brightness correction and dispersion correction of images. Further, the data processor 223 performs various types of image processing and analysis on images (anterior segment image, etc.) acquired using the anterior segment observation system 5.

The data processor 223 can form volume data (voxel data) of the subject's eye E by performing known image processing such as interpolation processing for interpolating pixels between tomographic images. In the case of displaying an image based on the volume data, the data processor 223 performs a rendering processing on the volume data so as to form a pseudo three-dimensional image viewed from a specific line-of-sight direction.

The data processor 223 can form a B-mode image (longitudinal cross-sectional image, axial cross-sectional image) in an arbitrary cross section, a C-mode image (transverse section image, horizontal cross-sectional image) in an arbitrary cross section, a projection image, a shadowgram, etc., by performing various renderings on the acquired volume data (three-dimensional data set, stack data, etc.). An image in an arbitrary cross section such as the B-mode image or the C-mode image is formed by selecting pixels (voxels) on a designated cross section from the three-dimensional data set. The projection image is formed by projecting the three-dimensional data set in a predetermined direction (Z direction, depth direction, axial direction). The shadowgram is formed by projecting a part of the three-dimensional data set (for example, partial data corresponding to a specific layer) in a predetermined direction. An image having a viewpoint on the front side of the subject's eye, such as the C-mode image, the projection image, and the shadowgram, is called a front image (en-face image).

Further, the data processor 223 can build (form) the B-mode image or the front image (blood vessel emphasized image, angiogram) in which retinal blood vessels and choroidal blood vessels are emphasized (highlighted), based on data (for example, B scan image data) acquired in time series by OCT. For example, the OCT data in time series can be acquired by repeatedly scanning substantially the same site of the subject's eye E.

In some embodiments, the data processor 223 compares the B-scan images in time series acquired by B-scan for substantially the same site, converts the pixel value of a change portion of the signal intensity into a pixel value corresponding to the change portion, and builds the emphasized image in which the change portion is emphasized. Further, the data processor 223 forms an OCT angiogram by extracting information of a predetermined thickness at a desired site from a plurality of built emphasized images and building as an en-face image.

Further, the data processor 223 can determine the focus state of the measurement light LS in focus adjustment by analyzing the detection result of the interference light obtained by the OCT measurement, as a determination unit. For example, the main controller 211 performs repetitive OCT measurements while controlling the movement of the focusing lens 87 according to a predetermined algorithm. The data processor 223 analyzes detection results of interference light LC repeatedly acquired by the OCT measurements to calculate predetermined evaluation values relating to image quality of images (OCT images) obtained by the OCT measurements. The data processor 223 determines whether the calculated evaluation value is equal to or less than a threshold. In some embodiments, the focus adjustment is continued until the calculated evaluation value becomes equal to or less than the threshold. That is, when the evaluation value is equal to or less than the threshold, it is determined that the focus state of the measurement light LS is appropriate. And the focus adjustment is continued until it is determined that the focus state of the measurement light LS is appropriate.

In some embodiments, the main controller 211 monitors the intensity of the interference signal (interference intensity, interference sensitivity) acquired sequentially while acquiring the interference signal by performing the repetitive OCT measurement described above. In addition, while performing this monitoring process, the focusing lens 87 is moved to find the position of the focusing lens 87 in which the interference intensity is maximized. With the focus adjustment thus performed, the focusing lens 87 can be moved to the position where the interference intensity is optimized.

Further, the data processor 223 can determine the polarization state of at least one of the measurement light LS and the reference light LR by analyzing the detection result of the interference light obtained by the OCT measurement. For example, the main controller 211 performs repetitive OCT measurements while controlling at least one of the polarization controllers 103 and 118 according to a predetermined algorithm. In some embodiments, the main controller 211 controls the attenuator 120 to change an attenuation of the reference light LR. The data processor 223 analyzes detection results of interference light LC repeatedly acquired by the OCT measurements to calculate predetermined evaluation values relating to image quality of OCT images. The data processor 223 determines whether the calculated evaluation value is equal to or less than a threshold. The threshold is set in advance. Polarization adjustment is continued until the evaluation value calculated becomes equal to or less than the threshold. That is, when the evaluation value is equal to or less than the threshold, it is determined that the polarization state of the measurement light LS is appropriate. And the polarization adjustment is continued until it is determined that the polarization state of the measurement light LS is appropriate.

In some embodiments, the main controller 211 can monitor the interference intensity also in the polarization adjustment.

Further, the data processor 223 performs predetermined analysis processing on the detection result of the interference light acquired by the OCT measurement or the OCT image formed based on the detection result. Examples of the predetermined analysis processing include specifying (identification) of a predetermined site (tissue, lesion) of the subject's eye E; calculation of a distance between designated sites (distance between layers, interlayer distance), area, angle, ratio, or density; calculation by a designated formula; specifying of the shape of a predetermined site; calculation of these statistics; calculation of distribution of the measured value or the statistics; image processing based on these analysis processing results, and the like. Examples of the predetermined tissue include a blood vessel, an optic papilla, a central fovea, a macula, and the like. Examples of the predetermined lesion include a leukoma, a hemorrhage, and the like.

The data processor 223 that functions as described above includes, for example, the aforementioned microprocessor, RAM, ROM, hard disk drive, circuit board, and the like. Computer programs that cause a microprocessor to execute the above functions are previously stored in a storage device such as a hard disk drive.

(Display Unit 270, Operation Unit 280)

Upon receiving control of the controller 210, the display unit 270 displays information, as a user interface unit. The display unit 270 includes the display unit 10 as illustrated in FIG. 1 and the like.

The operation unit 280 is used to operate the ophthalmologic apparatus, as the user interface unit. The operation unit 280 includes various types of hardware keys (the joystick, buttons, switches, etc.) provided in the ophthalmologic apparatus. Further, the operation unit 280 may include various kinds of software keys (buttons, icons, menus, etc.) displayed on the touch panel type display screen 10a.

At least part of the display unit 270 and the operation unit 280 may be integrally configured. A typical example of this is the touch-panel display screen 10a.

(Communication Unit 290)

The communication unit 290 has the function of communicating with an external device (not shown). The communication unit 290 includes a communication interface according to the mode of communication with an external device. Examples of the external device includes an eyeglass lens measurement device for measuring the optical properties of lenses. The eyeglass lens measurement device measures the power of the eyeglass lens worn by the subject and inputs the measurement data to the ophthalmologic apparatus 1000. The external device may also be a device (reader) having the function of reading information from a recording medium or a device (writer) having the function of writing information to a recording medium. Further, the external device may be a hospital information system (HIS) server, a Digital Imaging and Communications in Medicine (DICOM) server, a doctor terminal, a mobile terminal, a personal terminal, a cloud server, or the like. The communication unit 290 may be provided in the processing unit 9, for example.

Operation Example

The operation of the ophthalmologic apparatus 1000 according to the first embodiment will be described.

Figure 5:
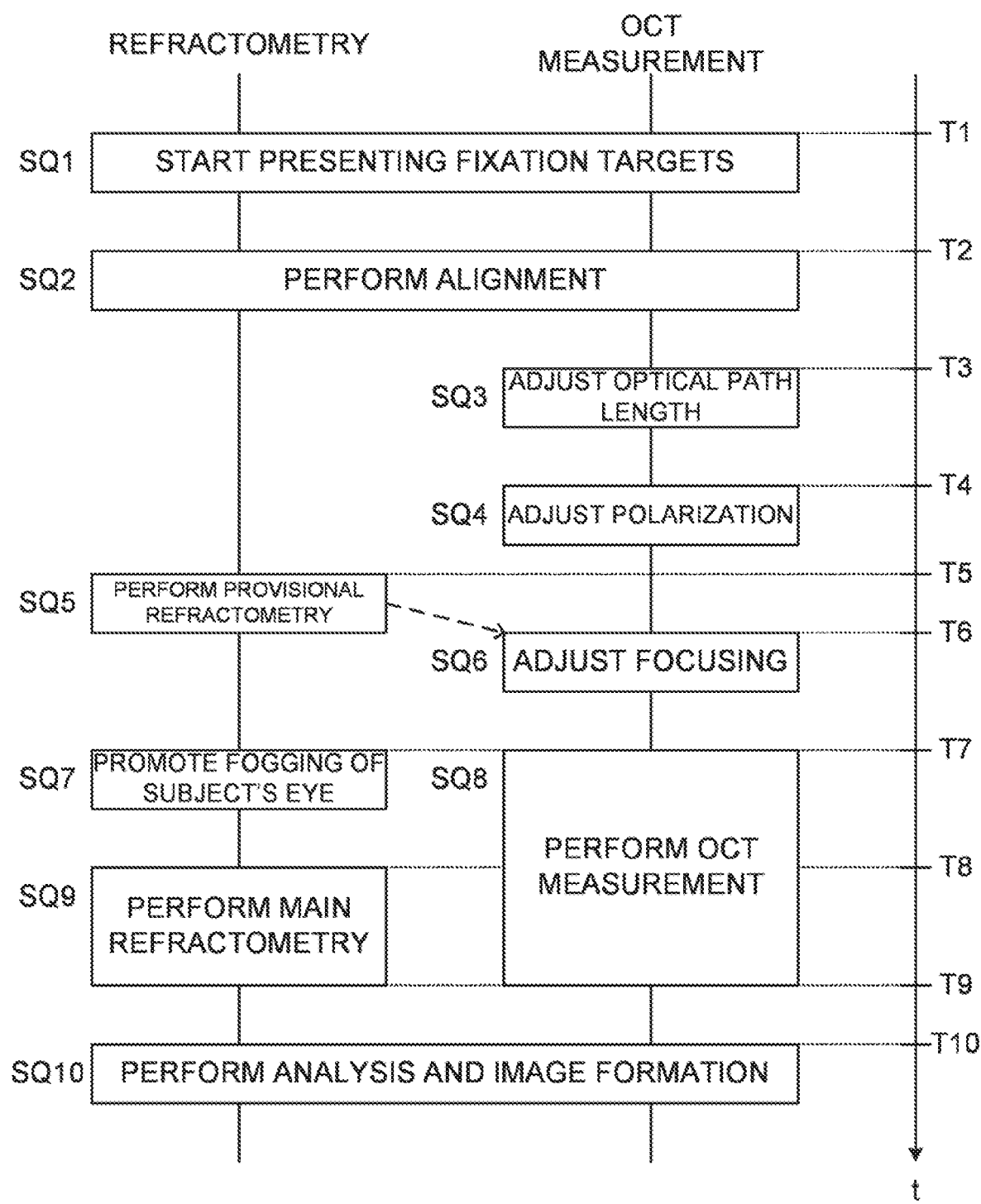
FIG. 5 is a schematic diagram illustrating an example of an operation of the ophthalmologic apparatus according to the first embodiment.

FIG. 5 illustrates an example of the operation of the ophthalmologic apparatus 1000. FIG. 5 shows a flowchart of an example of the operation of the ophthalmologic apparatus 1000 in the case of simultaneously performing refractometry and OCT measurement. It should be noted that FIG. 5 schematically shows not only the example of the operation of each of the refractometry and the OCT measurement, but also the performing timing of each step of the refractometry and the OCT measurement which are simultaneously performed. The storage unit 212 stores a of computer programs for realizing the processing shown in FIG. 5. The main controller 211 operates according to the computer programs, and thereby the main controller 211 performs the processing shown in FIG. 5.

(SQ1: Start Presenting Fixation Targets)

When the examiner performs a predetermined operation on the operation unit 280 in a state where the face of the subject is fixed to a face supporter (not shown), the ophthalmologic apparatus 1000 starts simultaneously presenting the fixation target for the refractometry and the fixation target for the OCT measurement to the subject's eye E at time T1.

Specifically, the main controller 211 controls the first fixation target projection system 41A and the second fixation target projection system 41B to start presenting the fixation targets FT1 and FT2 shown in FIGS. 4A and 4B substantially simultaneously. Thereby, presenting the fixation target FT3 shown in FIG. 4C to the subject's eye E is started.

(SQ2: Perform Alignment)

Sequentially, the main controller 211 performs alignment at time T2.

Specifically, the main controller 211 turns on the Z alignment light source 11 and the XY alignment light source 21. Furthermore, the main controller 211 turns on the anterior segment illumination light source 50. The processing unit 9 acquires imaging signal of an anterior segment image formed on the imaging surface of the imaging element 59 and controls the display unit 270 to display the anterior segment image. After that, the optical system shown in FIG. 1 is moved to at the inspection position of the subject's eye E. The inspection position is a position where the inspection of the subject's eye E can be performed with sufficient accuracy. The subject's eye E is placed at the inspection position through the alignment described above (that is, by the use of the Z alignment system 1, the XY alignment system 2, and the anterior segment observation system 5). The movement of the optical system is performed by the controller 210 according to operation or instruction from a user, or instruction by the controller 210. That is, the movement of the optical system to the inspection position of the subject's eye E and the preparation for the objective measurement are carried out.

Further, the main controller 211 moves the refractometry light source 61, the focusing lens 74, and the fixation unit 40 along the respective optical axes to the origin positions (for example, the position corresponding to OD).

(SQ3: Adjust Optical Path Length)

Next, the main controller 211 performs the adjustment of the optical path length at time T3.

For example, in a whole eye mode in which the OCT measurement is performed in a range including the cornea to the retina or in an anterior segment mode in which the OCT measurement of the anterior segment is performed, the main controller 211 adjusts the optical path length difference between the measurement light LS and the reference light LR so as to match a predetermined optical path length difference by controlling the movement mechanism for moving the corner cube 114.

For example, in a fundus mode in which the OCT measurement of the fundus (retina) is performed, the optical path length difference between the measurement LS and the reference light LR is adjusted so that the fundus Ef is depicted at a desired depth position in the tomographic image. For example, the main controller 211 controls the OCT optical system 8 to perform OCT provisional measurement and controls the image forming unit 222 to form a tomographic image for adjustment. That is, the main controller 211 controls the optical scanner 88 to deflect the measurement light LS generated based on the light L0 emitted from the OCT light source 101 and to scan the predetermined site (for example, fundus) of the subject's eye E with the deflected measurement light LS. The detection result of the interference light obtained by scanning with the measurement light LS is sent to the image forming unit 222 after being sampled in synchronization with the clock KC. The image forming unit 222 forms a tomographic image (OCT image) of the subject's eye E from the obtained interference signal.

The main controller 211 controls the data processor 223 to specify the predetermined site (for example, fundus) in the obtained tomographic image. The main controller 211 adjusts the optical path length difference between the measurement light LS and the reference light LR by controlling the movement mechanism for moving the corner cube 114 so that a Z position of the specified predetermined site is a predetermined depth position of the frame of the tomographic image. In some embodiments, the optical path length difference between the measurement light LS and the reference light LR is adjusted by changing the optical path length of the measurement light LS.

(SQ4: Adjust Polarization)

Next, the main controller 211 adjusts the polarization at time T4.

Specifically, the main controller 211 controls at least one of the polarization controllers 103 and 118 to change the polarization state of at least one of the light L0 and the measurement light LS by a predetermined amount. After that, the main controller 211 controls the OCT optical system 8 to perform OCT measurement and controls the image forming unit 222 to form the OCT image based on the acquired detection result of the interference light. The main controller 211 controls the data processor 223 to determine the image quality of the OCT image acquired by the OCT measurement. When it is determined that the polarization state is not appropriate based on the determination result of the data processor 223, the main controller 211 controls the polarization controllers 103 and 118 again and repeats this until it is determined that the polarization state of the measurement light LS is appropriate.

(SQ5: Perform provisional refractometry)

Next, the main controller 211 performs the provisional measurement of the refractive power at time T5. In the provisional measurement, the positions of the refractometry optical system and the OCT optical system 8 or the like are adjusted before the main measurement (definitive measurement, non-provisional measurement).

For example, the main controller 211 projects the ring-shaped measurement pattern light flux for refractometry onto the subject's eye E as described before. The ring image based on the returning light of the measurement pattern light flux from the subject's eye E is imaged on the imaging surface of the imaging element 59. The main controller 211 determines whether or not the ring image based on the returning light from the fundus Ef detected by the imaging element 59 can be acquired. For example, the main controller 211 detects a position (pixel) of the edge of the image that is formed based on the returning light detected by the imaging element 59, and determines whether or not the width (difference between outer diameter and inner diameter) of the image is greater than or equal to a predetermined value. Alternatively, the main controller 211 may determine whether or not the ring image can be acquired by determining whether or not a ring can be formed based on points (image) having a predetermined height (ring diameter) or more.

When it is determined that the ring image can be acquired, the eye refractive power calculator 221 analyzes the ring image based on the returning light of the measurement pattern light flux projected onto the subject's eye E by a known method, and calculates a provisional spherical power S and a provisional astigmatic power C. Based on the obtained provisional spherical power S and the obtained provisional astigmatic power C, the main controller 211 sets the refractometry light source 61, the focusing lens 74, and the fixation unit 40 to respective positions of the equivalent spherical power (S+C/2) (positions corresponding to a provisional far point).

When it is determined that the ring image can not be acquired, the main controller 211 moves the refractometry light source 61 and the focusing lens 74 to the minus power side (for example, −10 D) or the plus power side (for example, +10 D) in a preset step, considering the possibility of high refractive error of the eye. The main controller 211 controls the refractometry light reception system 7 to detect the ring image at each position. If it is still determined that the ring image can not be acquired, the main controller 211 executes a predetermined measurement error process. In this case, the operation of the ophthalmologic apparatus 1000 may proceed to nest step. In the controller 210, information indicating that the result of refractometry can not be acquired is stored in the storage unit 212.

(SQ6: Adjust Focusing)

Next, the main controller 211 adjusts the focusing in the OCT optical system 8 at time T6.

For example, in the whole eye mode or the anterior segment mode, the main controller 211 moves the focusing lens 87 to a predetermined position so that the focal position of the measurement light LS is disposed near the center of the crystalline lens. After alignment is completed, the position where the focusing lens 87 should be disposed is uniquely specified based on the working distance of the ophthalmologic apparatus 1000 and the configuration of the optical system.

For example, in the whole eye mode or the fundus mode, the main controller 211 moves the focusing lens 87 to a position corresponding to the obtained equivalent spherical power by the provisional refractometry in step SQ5 so that the focal position of the measurement light LS is disposed near the fundus. Further, the main controller 211 controls the OCT optical system 8 to perform the OCT measurement after moving the focusing lens 87 by a predetermined distance for the focus fine adjustment. The main controller 211 controls the data processor 223 to determine the focus state of the measurement light LS based on the detection result of the interference light acquired by the OCT measurement. When it is determined that the focus state is not appropriate based on the determination result of the data processor 223, the main controller 211 controls the movement of the focusing lens 87 again and repeats this until it is determined that the focus state of the measurement light LS is appropriate.

(SQ7: Promote Fogging of Subject's Eye)

Next, the main controller 211 performs the fogging control at time T7.

Specifically, the main controller 211 moves the fixation unit 40 by a predetermined diopter (for example, 1.5 diopters) from the position of the equivalent spherical power obtained in step SQ6. Thereby, the visual target chart 43A in the fixation unit 40 can be disposed at a position where the fogging of the subject's eye E is promoted.

(SQ8: Perform OCT Measurement)

The main controller 211 starts the OCT measurement at time T7 after focus adjustment in step SQ6 is completed. Thereby, the fogging control in step SQ7 and the OCT measurement are performed substantially simultaneously. In case that a three-dimensional scan is performed in step SQ8, the main refractometry and the OCT measurement can be terminated substantially simultaneously by simultaneously performing steps SQ7 and SQ8.

In step SQ8, the main controller 211 turns on the OCT light source 101 and controls the optical scanner 88 to scan the predetermined site of the fundus Ef with the measurement light LS. A detection signal obtained by scanning with the measurement light LS is fed to the image forming unit 222.

In some embodiments, the OCT measurement in step SQ8 is performed after the fogging control in step SQ7 is completed. That is, in case that a two-dimensional scan such as a line scan or a radial scan is performed in step SQ8, step SQ8 and step SQ9 described later are simultaneously started.

(SQ9: Perform Main Refractometry)

The main controller 211 starts the main refractometry at time T8 after the fogging control in step SQ7 is completed. Thereby, the main refractometry and the OCT measurement are performed simultaneously.

The main controller 211 controls the refractometry projection system 6 and the refractometry light reception system 7 to acquire a ring image again as the main measurement. The main controller 211 controls the eye refractive power calculator 221 to calculate a spherical power, an astigmatic power, and an astigmatic axis angle from the result obtained by analyzing the ring image acquired in the same manner as described above and the movement amount of the focusing lens 74.

Further, the eye refractive power calculator 221 obtains a position corresponding the far point of the subject's eye E (position corresponding to the far point obtained by the main measurement) from the obtained spherical power and the obtained astigmatic power. The main controller 211 moves the fixation unit 40 to the position corresponding to the obtained far point. In the controller 210, the position of the focusing lens 74, the calculated spherical power, and the like are stored in the storage unit 212. Upon reception of an instruction from the main controller 211, an operation or instruction on the operation unit 280 by the user, the operation of the ophthalmologic apparatus 1000 proceeds to step SQ10.

In some embodiments, the main measurement in step SQ9 and the OCT measurement in step SQ8 are terminated substantially simultaneously (for example, at time T9).

(SQ10: Perform Analysis and Image Formation)

Next, the main controller 211 controls the data processor 223 to perform analysis processing on the spherical power and the like obtained in step SQ9 and the result of the OCT measurement in step SQ8, at time T10. Further, the main controller 211 controls the image forming unit 222 or the data processor 223 to perform image forming processing based on the result of the OCT measurement obtained in step SQ8. This terminates the operation of the ophthalmologic apparatus 1000.

As described above, the refractometry optical system and the OCT optical system 8 are wavelength-separated and two fixation targets having different visual angles are simultaneously presented to the subject's eye E. Therefore, the refractometry and the OCT measurement can be simultaneously performed. Thereby, the time for inspection can be shorted and the burden on the subject can be significantly reduced.

Second Embodiment

In the first embodiment, the case has been described in which the fixation target for refractometry and the fixation target for OCT measurement are moved independently. However, the configuration of the ophthalmologic apparatus according to the embodiments is not limited thereto. For example, in the case that the spot size of the light from the fixation light source projecting the fixation target for OCT measurement is sufficiently small, the fixation target for OCT measurement can be moved integrally with the fixation target for refractometry. Hereinafter, the ophthalmologic apparatus according to the second embodiment is described below mainly about the differences from the first embodiment.

Figure 6A:
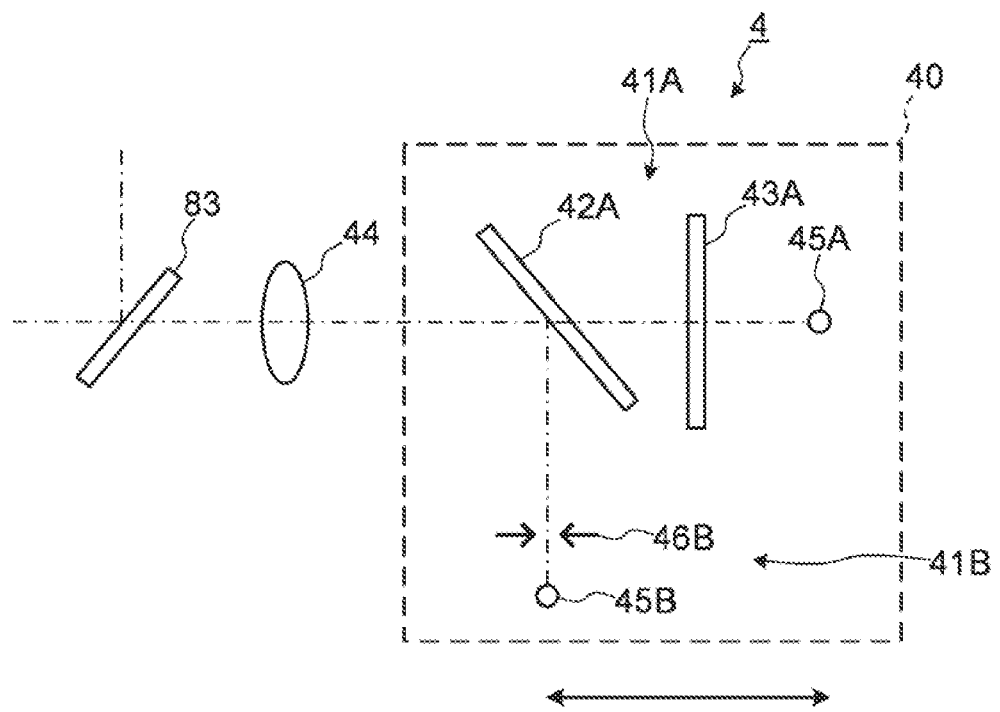
FIG. 6A is a schematic diagram illustrating an example of a configuration of an optical system of an ophthalmologic apparatus according to a second embodiment.

FIG. 6A shows an example of the configuration of the fixation unit 40 according to the second embodiment. In FIG. 6A, parts similarly configured to those in FIG. 1 are denoted by the same reference numerals, and the description thereof is omitted unless it is necessary.

The first fixation target projection system 41A includes a half mirror 42A, a transmission type visual target chart 43A, and an illumination light source 45A. The visual target chart 43A, the half mirror 42A, and the relay lens 44 are arranged in this order from the illumination light source 45A toward the dichroic mirror 83. The visual target chart 43A is arranged between the illumination light source 45A and the subject's eye E. The visual target chart 43A is the transmissive visual target chart on which a landscape chart such as the fixation target FT1 is displayed. In some embodiment, the visual target chart 43A is a transparent film on which a landscape chart is printed.

The second fixation target projection system 41B includes a fixation light source 45B and a diaphragm 46B. The diaphragm 46B is arranged between the fixation light source 45B and the half mirror 42A. In some embodiments, the diaphragm 46B is arranged at the pupil conjugate position. In some embodiments, the fixation light source 45B and the visual target chart 43A are arranged at positions optically conjugate with each other. In some embodiments, the visual target chart are arranged between the diaphragm 46B and the half mirror 42A. The visual target chart is a transmissive visual target chart on which a dot visual target or a cross visual target such as the fixation target FT1 is represented. In some embodiments, the visual target chart is a transparent film on which the dot visual target is printed.

The main controller 211 turns on the illumination light source 45A to illuminate the visual target chart 43A with light from the illumination light source 45A when the refractometry is performed. Light penetrating the visual target chart 43A is transmitted through the half mirror 42A. The landscape chart is projected onto the subject's eye E by irradiating the subject's eye E with the fixation light flux transmitted through the half mirror 42A. Further, the main controller 211 turns on the fixation light source 45B when the OCT measurement is performed. Thereby, the fixation light flux passing through the aperture formed in the diaphragm 46B is reflected by the half mirror 42A and is projected onto the subject's eye E as the bright spot (dot visual target) (second fixation target). The main controller 211 can project the fixation target FT3 shown in FIG. 4C onto the subject's eye E by simultaneously turning on the illumination light source 45A and the fixation light source 45B.

In some embodiments, the main controller 211 constantly turns on the illumination light source 45A and blinks the fixation light source 45B. Thereby, the presentation state of the fixation target FT2 (bright spot BP1) is changed. In some embodiments, the fixation light source 45B is movable with respect to the optical axis. In some embodiments, the half mirror 42A can change the direction of the reflecting surface with respect to the optical axis of the fixation projection system 4. In some embodiments, a plurality of fixation light sources 45B are provided. The main controller 211 selectively turns on the plurality of fixation light source 45B to change or move the projection position of the bright spot. In some embodiments, the main controller 211 can change the brightness and the depth of focus of the bright spot by changing the aperture size of the diaphragm 46B.

An example of the operation of the ophthalmologic apparatus according to the second embodiment is the same as FIG. 5. Therefore, the detailed description is not repeated here.

Figure 6B:
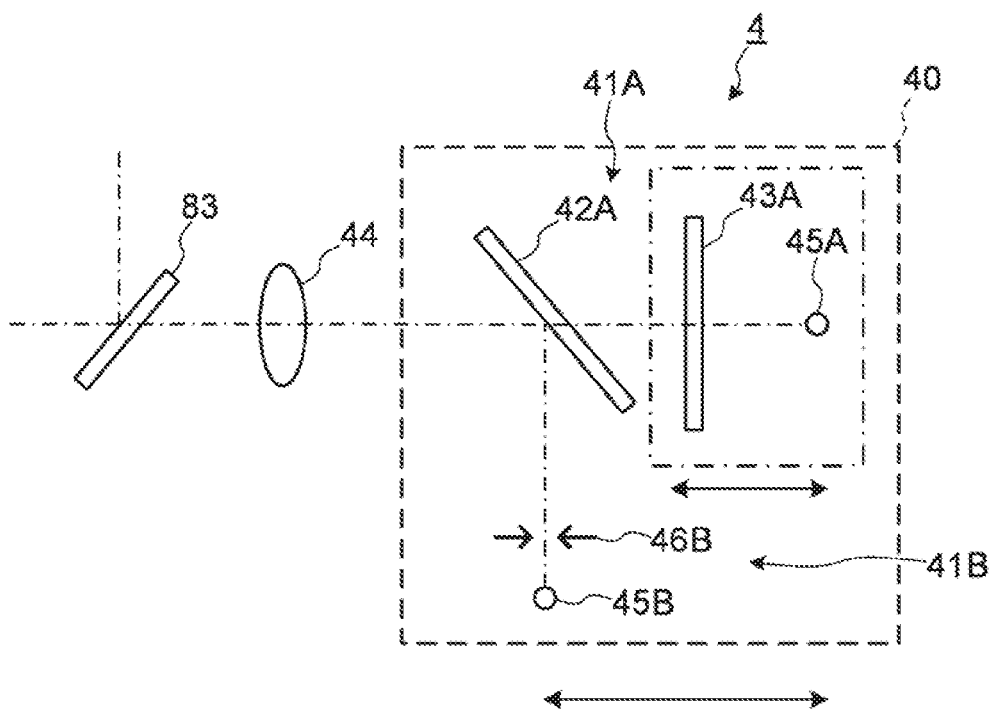
FIG. 6B is a schematic diagram illustrating another example of a configuration of the optical system of the ophthalmologic apparatus according to the second embodiment.

In the second embodiment, the visual target chart 43A and the illumination light source 45A may be moved integrally along the optical path, as shown in FIG. 6B. In some embodiments, the visual target chart 43A is moved alone along the optical path. In FIG. 6B, the visual target chart 43A and the illumination light source 45A can be moved integrally to a position where the fogging of the subject's eye is promoted with the position of the fixation light source 45B fixed. In some embodiments, the visual target chart 43A and the illumination light source 45A are integrally moved along the optical path by 1.5 diopters after the fixation light source 45B and the visual target chart 43A are arranged at the fundus conjugate position by moving the fixation unit 40.

As described above, according to the second embodiment, as in the first embodiment, two fixation targets having different visual angles are simultaneously presented to the subject's eye E. Therefore, the refractometry and the OCT measurement can be simultaneously performed. Thereby, the time for inspection can be shorted and the burden on the subject can be significantly reduced.

Third Embodiment

The configuration of the fixation projection system 4 according to the embodiments is not limited to the configuration explained in the first embodiment or the second embodiment. Hereinafter, the ophthalmologic apparatus according to the third embodiment is described below mainly about the differences from the second embodiment.

Figure 7:
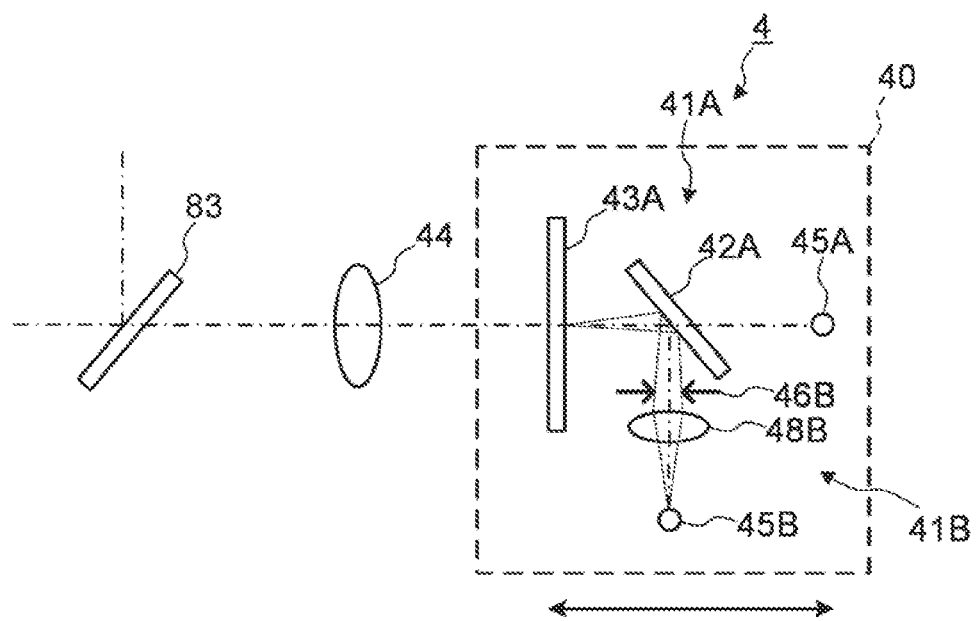
FIG. 7 is a schematic diagram illustrating an example of a configuration of an optical system of an ophthalmologic apparatus according to a third embodiment.

FIG. 7 shows an example of the configuration of the fixation unit 40 according to the third embodiment. In FIG. 7, parts similarly configured to those in FIG. 1 or FIG. 6A are denoted by the same reference numerals, and the description thereof is omitted unless it is necessary.

The first fixation target projection system 41A includes the half mirror 42A, the transmission type visual target chart 43A, and the illumination light source 45A. The half mirror 42A, the visual target chart 43A, and the relay lens 44 are arranged in this order from the illumination light source 45A toward the dichroic mirror 83.

The second fixation target projection system 41B includes the fixation light source 45B, the diaphragm 46B, and a relay lens 48B. The relay lens 48B is arranged between the fixation light source 45B and the diaphragm 46B. In some embodiment, the relay lens 48B is movable in the optical axis direction. Thereby, the fixation light source 45B can be disposed at the fundus conjugate position independently of the first fixation target projection system 41A.

The main controller 211 turns on the illumination light source 45A when the refractometry is performed. Light from the illumination light source 45A is transmitted through the half mirror 42A and illuminates the visual target chart 43A. The landscape is projected onto the subject's eye E by irradiating the subject's eye E with the fixation light flux transmitted through the visual target chart 43A. Further, the main controller 211 turns on the fixation light source 45B when the OCT measurement is performed. Light from the fixation light source 45B passes through the relay lens 48B and the fixation light flux passing through the aperture formed in the diaphragm 46B is reflected by the half mirror 42A, is transmitted through the visual target chart 43A, and is projected onto the subject's eye E as the bright spot (dot visual target) (second fixation target). The main controller 211 can project the fixation target FT3 shown in FIG. 4C onto the subject's eye E by simultaneously turning on the illumination light source 45A and the fixation light source 45B.

In some embodiments, the main controller 211 constantly turns on the illumination light source 45A and blinks the fixation light source 45B. Thereby, the presentation state of the fixation target FT2 (bright spot BP1) is changed. In some embodiments, the fixation light source 45B is movable with respect to the optical axis. In some embodiments, the half mirror 42A can change the direction of the reflecting surface with respect to the optical axis of the fixation projection system 4. In some embodiments, a plurality of fixation light sources 45B are provided. The main controller 211 selectively turns on the plurality of fixation light source 45B to change or move the projection position of the bright spot. In some embodiments, the main controller 211 can change the brightness and the depth of focus of the bright spot by changing the aperture size of the diaphragm 46B.

An example of the operation of the ophthalmologic apparatus according to the third embodiment is the same as FIG. 5. Therefore, the detailed description is not repeated here.

As described above, according to the third embodiment, as in the second embodiment, two fixation targets having different visual angles are simultaneously presented to the subject's eye E. Therefore, the refractometry and the OCT measurement can be simultaneously performed. Thereby, the time for inspection can be shorted and the burden on the subject can be significantly reduced.

Fourth Embodiment

The configuration of the fixation projection system 4 according to the embodiments is not limited to the configuration explained in the first to the third embodiments. Hereinafter, the ophthalmologic apparatus according to the fourth embodiment is described below mainly about the differences from the second embodiment.

Figure 8:
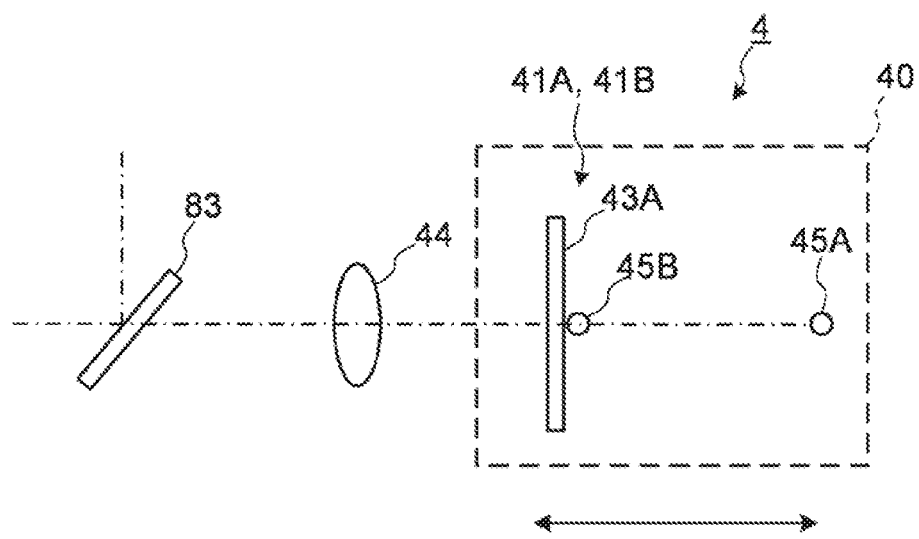
FIG. 8 is a schematic diagram illustrating an example of a configuration of an optical system of an ophthalmologic apparatus according to a fourth embodiment.

FIG. 8 shows an example of the configuration of the fixation projection system 4 according to the fourth embodiment. In FIG. 8, parts similarly configured to those in FIG. 1 or FIG. 6A are denoted by the same reference numerals, and the description thereof is omitted unless it is necessary.

The first fixation target projection system 41A includes the transmission type visual target chart 43A and the illumination light source 45A. The visual target chart 43A is arranged between the illumination light source 45A and the relay lens 44.

The second fixation target projection system 41B includes the fixation light source 45B. The fixation light source 45B is disposed on the back side of the visual target chart 43A. That is, the fixation light source 45B and the visual target chart 43A are arranged in this order from the illumination light source 45A toward the relay lens 44. In some embodiments, the fixation light source 45B is a point light source having a predetermined light emission size.

The main controller 211 turns on the illumination light source 45A to illuminate the visual target chart 43A with light from the illumination light source 45A when the refractometry is performed. Thereby, the landscape chart is projected onto the subject's eye E. Further, the main controller 211 turns on the fixation light source 45B when the OCT measurement is performed. Thereby, the bright spot (dot visual target) is projected onto the subject's eye E. The main controller 211 can project the fixation target FT3 shown in FIG. 4C onto the subject's eye E by simultaneously turning on the illumination light source 45A and the fixation light source 45B.

In some embodiments, the main controller 211 constantly turns on the illumination light source 45A and blinks the fixation light source 45B. Thereby, the presentation state of the fixation target FT2 (bright spot BP1) is changed. In some embodiments, the fixation light source 45B is movable with respect to the optical axis. In some embodiments, the half mirror 42A can change the direction of the reflecting surface with respect to the optical axis of the fixation projection system 4. In some embodiments, a plurality of fixation light sources 45B are provided. The main controller 211 selectively turns on the plurality of fixation light source 45B to change or move the projection position of the bright spot.

An example of the operation of the ophthalmologic apparatus according to the fourth embodiment is the same as FIG. 5. Therefore, the detailed description is not repeated here.

As described above, according to the fourth embodiment, as in the first embodiment, two fixation targets having different visual angles are simultaneously presented to the subject's eye E. Therefore, the refractometry and the OCT measurement can be simultaneously performed. Thereby, the time for inspection can be shorted and the burden on the subject can be significantly reduced.

In the first to fourth embodiments, the cases have been described in which the refractometry and the OCT measurement are performed simultaneously. However, the operation of the ophthalmologic apparatus according to the embodiments is not limited thereto. For example, the ophthalmologic apparatus according to the embodiments may simultaneously perform the keratometry and the OCT measurement as in the above embodiments. In the keratometry, the fixation target similar to the refractometry may be presented to the subject's eye E.

The refractometry projection system 6 and the refractometry light reception system 7 are an example of the "refractive power measurement optical system" according to the embodiments. The landscape chart is an example of the "first fixation target" according to the embodiments. The dot visual target (bright spot) or the cross visual target is an example of the "second fixation target" according to the embodiments. The half mirror 42A is an example of the "optical member" according to the embodiments. The illumination light source 45A is an example of the "first light source" according to the embodiments. The fixation light source 45B is an example of the "light source" or the "second light source" according to the embodiments. The fixation light source 45B is an example of the "light source" according to the embodiments. The dichroic mirror 67 is an example of the "optical path combining and separating member" according to the embodiments.

[Actions and Effects]

Described below are the actions and effects of the ophthalmologic apparatus according to the embodiments.

An ophthalmologic apparatus (1000) according to some embodiments includes a refractometry optical system (refractometry projection system 6, refractometry light reception system 7), an OCT optical system (8), a fixation projection system (4), and a controller (210, main controller 211). The refractometry optical system projects light onto a subject's eye (E) and detects returning light from the subject's eye. The OCT optical system splits light (L0) from an OCT light source (101) into measurement light (LS) and reference light (LR), projects the measurement light onto the subject's eye, and detects interference light (LC) between returning light of the measurement light from the subject's eye and the reference light. The fixation projection system simultaneously projects a first fixation target (landscape chart) and a second fixation target (dot visual target, cross visual target) onto the subject's eye, a visual angle of the second fixation target being narrower than a visual angle of the first fixation target. The controller controls the refractometry optical system and the OCT optical system to simultaneously perform a refractometry and an OCT measurement.

According to such a configuration, two fixation targets having different visual angles can be simultaneously presented to the subject's eye. For example, the two fixation targets include a fixation target with a large visual angle so as not to allow the subject's eye to accommodate in the refractometry and a fixation target with a small visual angle so as to stabilize fixation in the OCT measurement. Since the refractometry and the OCT measurement are simultaneously performed while simultaneously presenting such fixation targets to the subject's eye, the time required for inspections and the like can be shorted while performing appropriate measurements and inspections in the ophthalmologic apparatuses including the refractometry optical system and the OCT optical system. Thereby, the burden on the subject can be significantly reduced.

In the ophthalmologic apparatus according to some embodiments, the controller controls the fixation projection system to change a presentation state of the second fixation target.

According to such a configuration, it is possible to cause the subject's eye to gaze at the second fixation target even when the first fixation target is projected onto the subject's eye.

In the ophthalmologic apparatus according to some embodiments, the fixation projection system includes a first fixation target projection system (41A) projecting the first fixation target onto the subject's eye and a second fixation target projection system (41B) projecting the second fixation target onto the subject's eye, and the first fixation target projection system includes an optical member (half mirror 42A) that combines an optical path of the second fixation projection system with an optical path of the first fixation target projection system.

According to such a configuration, the two fixation targets having different visual angles can be simultaneously presented to the subject's eye with a simple configuration.

In the ophthalmologic apparatus according to some embodiments, the first fixation target projection system includes a visual target chart (43A) on which the first fixation target is displayed and is disposed at a position where a fogging of the subject's eye is promoted, and the second fixation target projection system includes a light source (fixation light source 45B) disposed at an optically conjugate position with a fundus (Ef) of the subject's eye.

According to such a configuration, the first fixation target can be presented to the subject's eye so as not to allow the subject's eye to accommodate in the refractometry and the second fixation target can be presented to the subject's eye so as to stabilized fixation in the OCT measurement. Therefore, the highly accurate measurement result obtained by the refractometry and the highly accurate measurement result obtained by the OCT measurement can be simultaneously obtained.

In the ophthalmologic apparatus according to some embodiments, the first fixation target projection system includes a visual target chart (43A) on which the first fixation target is displayed, and the second fixation target projection system includes a light source (fixation light source 45B) disposed at an optically conjugate position with the visual target chart and a diaphragm (46B) arranged between the light source and the optical member.

According to such a configuration, the visual target chart, which is used for presenting the first fixation target and the second fixation target, and the light source can be integrally moved. Thereby, the refractometry and the OCT measurement can be simultaneously performed with a simple configuration.

In the ophthalmologic apparatus according to some embodiments, the first fixation target projection system includes a first light source (illumination light source 45A) and a transmissive visual target chart (43A) on which the first fixation target is displayed and is arranged on the side of the subject's eye with respect to the optical member, wherein the optical member is arranged between the first light source and the visual target chart, and the second fixation projection system includes a second light source (fixation light source 45B) disposed at an optically conjugate position with the visual target chart.

According to such a configuration, the visual target chart, which is used for presenting the first fixation target and the second fixation target, the first light source, and the second light source can be integrally moved. Thereby, the refractometry and the OCT measurement can be simultaneously performed with a simple configuration.

In the ophthalmologic apparatus according to some embodiments, the fixation projection system is movable in an optical axis direction, and the controller controls the fixation projection system to move the visual target chart to a position where a fogging of the subject's eye is promoted.

According to such a configuration, the fixation projection system for presenting the first fixation target and the second fixation target to the subject's eye can be moved with a simple configuration.

In the ophthalmologic apparatus according to some embodiments, the controller controls the OCT optical system to perform an OCT measurement while at least a fogging control for moving the visual target chart to a position where a fogging of the subject's eye is promoted is performed.

According to such a configuration, the time required for the inspections and the like can be greatly reduced by simultaneously performing the refractometry and the OCT measurement even when time is required for the OCT measurement, such as a three-dimensional scan.

The ophthalmologic apparatus according to some embodiments includes an optical path combining and separating member (dichroic mirror 67) that combines an optical path of the OCT optical system with an optical path of the refractometry optical system and an objective lens (51) disposed on an optical path combined by the optical path combining and separating member, wherein the optical path combining and separating member wavelength-separates light incident through the objective lens and guides the wavelength-separated light to the OCT optical system.

According to such a configuration, the refractometry and the OCT measurement can be simultaneously performed with a simple configuration.

A method of controlling an ophthalmologic apparatus (1000) according to some embodiments is a method of controlling the ophthalmologic apparatus including a refractometry optical system (refractometry projection system 6, refractometry light reception system 7), an OCT optical system (8), a fixation projection system (4), and a controller (210, main controller 211). The refractometry optical system projects light onto a subject's eye (E) and detects returning light from the subject's eye. The OCT optical system splits light (L0) from an OCT light source (101) into measurement light (LS) and reference light (LR), projects the measurement light onto the subject's eye, and detects interference light (LC) between returning light of the measurement light from the subject's eye and the reference light. The fixation projection system simultaneously projects a first fixation target (landscape chart) and a second fixation target (dot visual target, cross visual target) onto the subject's eye, a visual angle of the second fixation target being narrower than a visual angle of the first fixation target. The method of controlling the ophthalmologic apparatus includes a projection step that controls the fixation projection system to simultaneously project the first fixation target and the second fixation target onto the subject's eye and a measurement step that controls the refractometry optical system and the OCT optical system to simultaneously perform a refractometry and an OCT measurement while simultaneously projecting the first fixation target and the second fixation target onto the subject's eye.

According to such a control, since the refractometry and the OCT measurement are simultaneously performed while simultaneously presenting such fixation targets to the subject's eye, the time required for inspections and the like can be shorted while performing appropriate measurements and inspections in the ophthalmologic apparatuses including the refractometry optical system and the OCT optical system. Thereby, the burden on the subject can be significantly reduced.

In the method of controlling the ophthalmologic apparatus, the projection step controls the fixation projection system to change a presentation state of the second fixation target.

According to such a control, it is possible to cause the subject's eye to gaze at the second fixation target even when the first fixation target is projected onto the subject's eye.

In the method of controlling the ophthalmologic apparatus, the fixation projection system is movable in an optical axis direction, the fixation projection system includes a visual target chart (43A) on which the first fixation target is displayed, the measurement step includes a refractometry step that controls the refractometry optical system to perform the refractometry and an OCT measurement step that controls the OCT optical system to perform the OCT measurement, wherein the refractometry step includes a fogging control step that controls the fixation projection system to move the visual target chart to a position where a fogging of the subject's eye is promoted, and at least the fogging control step and the OCT measurement step are simultaneously performed.

According to such a control, the time required for the inspections and the like can be greatly reduced by simultaneously performing the refractometry and the OCT measurement even when time is required for the OCT measurement, such as a three-dimensional scan.

<Others>

The above-described embodiments are merely examples for carrying out the present invention. Those who intend to implement the present invention can apply any modification, omission, addition, or the like within the scope of the gist of the present invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmologic apparatus comprising:
a refractometry optical system configured to project light onto a subject's eye and to detect returning light from the subject's eye;
an OCT optical system configured to split light from an OCT light source into measurement light and reference light, to project the measurement light onto the subject's eye; and to detect interference light between returning light of the measurement light from the subject's eye and the reference light;

a fixation projection system configured to simultaneously project a first fixation target and a second fixation target onto the subject's eye; a visual angle of the second fixation target being narrower than a visual angle of the first fixation target; and a controller configured to control the refractometry optical system and the OCT optical system to simultaneously perform a refractometry and an OCT measurement, wherein the fixation projection system includes
a first fixation target projection system configured to project the first fixation target onto the subject's eye, and
a second fixation target projection system configured to project the second fixation target onto the subject's eye, and the first fixation target projection system further includes an optical member that combines an optical path of the second fixation projection system with an optical path of the first fixation target projection system, the first fixation target projection system and the second fixation target projection system are independently moveable in the optical axis directions, the first fixation target projection system is configured to project the first fixation target from a position where the fogging of the subject's eye is promoted, the second fixation target projection system is configured to project the second fixation target from the optically conjugate position with the fundus, and a wavelength range of the light in the refractometry optical system is different from a wavelength range of the light in the OCT optical system.

2. The ophthalmologic apparatus of claim 1, wherein the controller controls the fixation projection system to change a presentation state of the second fixation target.

3. The ophthalmologic apparatus of claim 1, wherein the first fixation target projection system includes a visual target chart on which the first fixation target is displayed and is disposed at a position where a fogging of the subject's eye is promoted, and the second fixation target projection system includes a light source disposed at an optically conjugate position with a fundus of the subject's eye.

4. The ophthalmologic apparatus of claim 3, wherein the controller controls the OCT optical system to perform an OCT measurement while at least a fogging control for moving the visual target chart to a position where a fogging of the subject's eye is promoted is performed.

5. The ophthalmologic apparatus of claim 1, wherein the first fixation target projection system includes a visual target chart on which the first fixation target is displayed, and the second fixation target projection system includes:
a light source disposed at an optically conjugate position with the visual target chart; and
a diaphragm arranged between the light source and the optical member.

6. The ophthalmologic apparatus of claim 1, wherein the first fixation target projection system includes:
a first light source; and
a transmissive visual target chart on which the first fixation target is displayed and is arranged on the side of the subject's eye with respect to the optical member, wherein the optical member is arranged between the first light source and the visual target chart, and the second fixation projection system includes a second light source disposed at an optically conjugate position with the visual target chart.

7. The ophthalmologic apparatus of claim 1, further comprising:

an optical path combining and separating member that combines an optical path of the OCT optical system with an optical path of the refractometry optical system; and an objective lens disposed on an optical path combined by the optical path combining and separating member, wherein the optical path combining and separating member wavelength-separates light incident through the objective lens and guides the wavelength-separated light to the OCT optical system.

8. A method of controlling an ophthalmologic apparatus, the ophthalmologic apparatus comprising:

a refractometry optical system configured to project light onto a subject's eye and to detect returning light from the subject's eye;

an OCT optical system configured to split light from an OCT light source into measurement light and reference light, to project the measurement light onto the subject's eye, and to detect interference light between returning light of the measurement light from the subject's eye and the reference light;

a fixation projection system configured to project a first fixation target and a second fixation target onto the subject's eye, a visual angle of the second fixation target being narrower than a visual angle of the first fixation target; and a controller, the method comprising:
a projection step that controls the fixation projection system to simultaneously project the first fixation target and the second fixation target onto the subject's eye;

a measurement step that controls the refractometry optical system and the OCT optical system to simultaneously perform a refractometry and an OCT measurement while simultaneously projecting the first fixation target and the second fixation target onto the subject's eye, wherein the fixation projection system includes
a first fixation target projection system configured to project the first fixation target onto the subject's eye, and
a second fixation target projection system configured to project the second fixation target onto the subject's eye, and the first fixation target projection system further includes an optical member that combines an optical path of the second fixation projection system with an optical path of the first fixation target projection system, and the first fixation target projection system and the second fixation target projection system are independently moveable in the optical axis directions, the projection step further includes the first fixation target projection system projecting the first fixation target from a position where the fogging of the subject's eye is promoted, and the second fixation target projection system projecting the second fixation target from the optically conjugate position with the fundus, and a wavelength range of the light in the refractometry optical system is different from a wavelength range of the light in the OCT optical system.

9. The method of controlling the ophthalmologic apparatus of claim 8, wherein the projection step controls the fixation projection system to change a presentation state of the second fixation target.

10. The method of controlling; the ophthalmologic apparatus of claim 8, wherein
the fixation projection system is movable in an optical axis direction,
the fixation projection system includes a visual target chart on which the first fixation target is displayed,
the measurement step includes:
a refractometry step that controls the refractometry optical system to perform the refractometry; and
an OCT measurement step that controls the OCT optical system to perform the OCT measurement,
wherein the refractometry step includes a fogging control step that controls the fixation projection system to move the visual target chart to a position where a togging of the subject's eye is promoted, and
at least the fogging control step and the OCT measurement step are simultaneously performed.

* * * * *